(12) United States Patent
Minn et al.

(10) Patent No.: US 9,375,002 B2
(45) Date of Patent: Jun. 28, 2016

(54) 5-AMINOPYRIMIDINE DERIVATIVES AND USE THEREOF FOR COMBATING UNDESIRED PLANT GROWTH

(71) Applicant: BAYER INTELLECTUAL PROPERTY GMBH, Monheim (DE)

(72) Inventors: Klemens Minn, Hattersheim (DE); Michael Gerhard Hoffmann, Floersheim (DE); Elmar Gatzweiler, Bad Nauheim (DE); Ines Heinemann, Hofheim (DE); Isolde Haeuser-Hahn, Leverkusen (DE); Christopher Hugh Rosinger, Hofheim (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/387,267

(22) PCT Filed: Mar. 27, 2013

(86) PCT No.: PCT/EP2013/056483
§ 371 (c)(1),
(2) Date: Sep. 23, 2014

(87) PCT Pub. No.: WO2013/144187
PCT Pub. Date: Oct. 3, 2013

(65) Prior Publication Data
US 2015/0094205 A1    Apr. 2, 2015

(30) Foreign Application Priority Data

Mar. 29, 2012 (EP) ..................... 12162187

(51) Int. Cl.
*A01N 43/54*    (2006.01)
*C07D 403/12*    (2006.01)
*C07D 401/12*    (2006.01)
*C07D 405/12*    (2006.01)
*C07D 239/42*    (2006.01)
*C07D 409/12*    (2006.01)
*C07D 239/47*    (2006.01)

(52) U.S. Cl.
CPC ............ *A01N 43/54* (2013.01); *C07D 239/42* (2013.01); *C07D 239/47* (2013.01); *C07D 401/12* (2013.01); *C07D 403/12* (2013.01); *C07D 405/12* (2013.01); *C07D 409/12* (2013.01)

(58) Field of Classification Search
CPC .. C07D 239/42; C07D 239/47; C07D 401/12; C07D 403/12; C07D 405/12; C07D 409/12; A01N 43/54
See application file for complete search history.

(56) References Cited

U.S. PATENT DOCUMENTS 8,329,717 B2    12/2012    Minn et al.
8,445,408 B2    5/2013    Minn et al.

FOREIGN PATENT DOCUMENTS

| EP | 00523533 A1 | 1/1993 | |
| GB | WO 2009081112 A2 * | 7/2009 | ............ A01N 43/54 |
| WO | WO 2009081112 A2 * | 7/2009 | |
| WO | 2010076009 A1 | 7/2010 | |
| WO | 2010076010 A1 | 7/2010 | |

OTHER PUBLICATIONS

L. M. Abell et al. Target-Site Directed Herbicide Design in, Pest Control With Enhanced Environmental Safety 15-37 (ACS Symposium Series; American Chemical Society, S. Duke, et al. eds, 1993).*
S.C. Knight et al., Annual Review of Phytopathology 35, 349-372, 357 (1997).*
W.T. Ruegg et al., Weed Research, 47(4), 271-275, 271 (2006).*
International Search Report from corresponding PCT/EP2013/056483, mailed Jun. 6, 2013.

* cited by examiner

*Primary Examiner* — Alexander R Pagano
(74) *Attorney, Agent, or Firm* — Bayer Intellectual Property GmbH

(57) ABSTRACT

What is described are compounds of the general formula (I) and agrochemically acceptable salts thereof

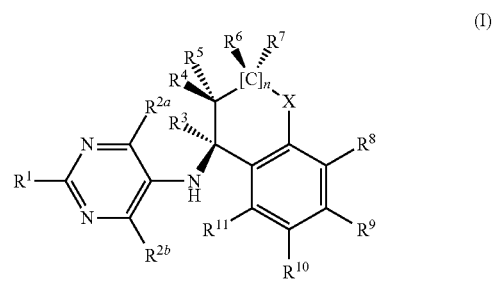

and their use in the field of crop protection.

18 Claims, No Drawings

5-AMINOPYRIMIDINE DERIVATIVES AND USE THEREOF FOR COMBATING UNDESIRED PLANT GROWTH

CROSS REFERENCE TO RELATED APPLICATIONS

This application is a §371 National Stage Application of PCT/EP2013/056483, filed Mar. 27, 2013, which claims priority to EP 12162187.4, filed Mar. 29, 2012.

BACKGROUND

1. Field of the Invention

The invention relates to the technical field of crop protection compositions, in particular that of herbicides for the selective control of broad-leaved weeds and weed grasses in crops of useful plants and in the ornamental garden and for the general control of broad-leaved weeds and weed grasses in areas of the environment where plant growth is disruptive.

2. Description of Related Art

In particular, the invention relates to substituted 5-aminopyrimidines, to processes for their preparation and to their use for controlling harmful plants.

Diaminopyrimidines having herbicidal action are known from the prior art. Thus, 2,4-diaminopyrimidines and their use in the field of crop protection are disclosed, for example, by the documents EP 0523533 A1, WO 2010/076009 and WO 2010/076010.

The use of the derivatives of this type as selective herbicides for controlling harmful plants or as plant growth regulators in various crops of useful plants, however, frequently requires an application rate associated with high costs, or results in unwanted damage to the useful plants. Moreover, in many cases the use of the active compounds is uneconomical owing to relatively high production costs.

It is therefore desirable to provide alternative chemical active compounds based on pyrimidine derivatives which can be used as herbicides or plant growth regulators and which are associated with certain advantages compared to systems known from the prior art.

SUMMARY

It is an object of the present invention to provide alternative pyrimidine derivatives which can be used as herbicides or plant growth regulators, having a satisfactory herbicidal action and a broad activity spectrum against harmful plants and/or having high selectivity in crops of useful plants.

Compared to the pyrimidine derivatives known from the prior art, these pyrimidine derivatives should display a better property profile, in particular better herbicidal activity against harmful plants, cover a broader spectrum of harmful plants and/or have higher selectivity in crops of useful plants.

According to the invention, we have now found specifically substituted 5-aminopyrimidines of the formula (I) which can be used advantageously as herbicides and plant growth regulators.

The compounds of the formula (I) according to the invention have, in the 5-position of the pyrimidine, a partially hydrogenated bicyclic substituent attached in the alpha-position to the aromatic ring via an amine.

The 5-aminopyridine derivatives of the formula (I) according to the invention differ from the known herbicides having a 2,4-diaminopyrimidine structure in the positioning and in the number of the amino groups. The 5-aminopyrimidines according to the invention are characterized in that they are substituted by only one amino group, where this amino group, which is substituted by a bicyclic radical, is located in the 5-position of the pyrimidine.

Thus, the radicals $R^1$, $R^{2a}$ and $R^{2b}$ in the compounds of the formula (I) do not represent an amino group, i.e. $R^1$, $R^{2a}$ and $R^{2b}$ are not attached via a nitrogen atom to the pyrimidine. However, the radicals $R^1$, $R^{2a}$ and $R^{2b}$ may still comprise an amino group or an amide group (e.g. aminocarbonyl-($C_1$-$C_6$)-alkyl, di-($C_1$-$C_6$)-alkylaminocarbonyl-($C_1$-$C_6$)-alkyl).

The present invention provides compounds of the formula (I)

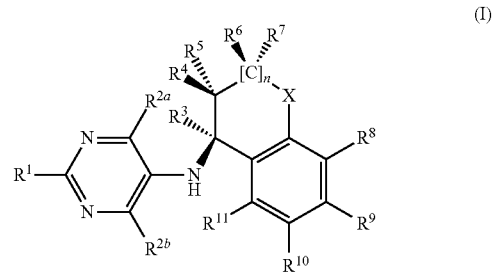

and their agrochemically acceptable salts in which
$R^1$ is selected from the group consisting of
cyano, nitro, C(O)OH, C(O)$NH_2$;
($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-haloalkylcarbonyloxy, ($C_1$-$C_6$)-alkylcarbonyl-($C_1$-$C_4$)-alkyl;
($C_1$-$C_6$)-alkoxy, ($C_1$-$C_6$)-haloalkoxy, ($C_1$-$C_6$)-alkoxycarbonyl, ($C_1$-$C_6$)-haloalkoxycarbonyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;
($C_2$-$C_6$)-alkenyl, ($C_2$-$C_6$)-haloalkenyl, ($C_2$-$C_6$)-alkenylcarbonyl, ($C_2$-$C_6$)-haloalkenylcarbonyl, ($C_2$-$C_6$)-alkenyloxy, ($C_2$-$C_6$)-haloalkenyloxy, ($C_2$-$C_6$)-alkenyloxycarbonyl, ($C_2$-$C_6$)-haloalkenyloxycarbonyl;
($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl;
tri-($C_1$-$C_6$)-alkylsilyl-($C_2$-$C_6$)-alkynyl, di-($C_1$-$C_6$)-alkylsilyl-($C_2$-$C_6$)-alkynyl, mono-($C_1$-$C_6$)-alkylsilyl-($C_2$-$C_6$)-alkynyl; phenylsilyl-($C_2$-$C_6$)-alkynyl;
($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl, each of which may be substituted at the aryl moiety by halogen, ($C_1$-$C_6$)-alkyl and/or ($C_1$-$C_6$)-haloalkyl;
($C_6$-$C_{14}$)-aryl-($C_1$-$C_6$)-alkyl, ($C_6$-$C_{14}$)-aryl-($C_1$-$C_6$)-alkoxy, ($C_6$-$C_{14}$)-aryl-($C_1$-$C_6$)-alkyl-carbonyl, ($C_6$-$C_{14}$)-aryl-($C_1$-$C_6$)-alkyl-carbonyloxy, ($C_6$-$C_{14}$)-aryl-($C_1$-$C_6$)-alkoxycarbonyl, ($C_6$-$C_{14}$)-aryl-($C_1$-$C_6$)-alkoxycarbonyloxy;
aminocarbonyl-($C_1$-$C_6$)-alkyl, di-($C_1$-$C_6$)-alkylaminocarbonyl-($C_1$-$C_6$)-alkyl;
mono-(($C_1$-$C_6$)-alkyl)-amino-carbonyl, mono-(($C_1$-$C_6$)-haloalkyl)-amino-carbonyl, di-(($C_1$-$C_6$)-alkyl)-amino-carbonyl, di-(($C_1$-$C_6$)-haloalkyl)-amino-carbonyl, (($C_1$-$C_6$)-alkyl-($C_1$-$C_6$)-haloalkyl)-amino-carbonyl, N—(($C_1$-$C_6$)-alkanoyl)-amino-carbonyl, N—(($C_1$-$C_6$)-haloalkanoyl)-amino-carbonyl, mono-(($C_6$-$C_{14}$)-aryl)-amino-carbonyl, di-(($C_6$-$C_{14}$)-aryl)-amino-carbonyl;

($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy;

($C_3$-$C_8$)-cycloalkyl which may optionally be substituted at the cycloalkyl radical by ($C_1$-$C_6$)-alkyl and/or halogen; ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-haloalkyl, ($C_3$-$C_8$)-cycloalkyl-($C_1$-$C_6$)-alkoxy, ($C_3$-$C_8$)-cycloalkyl-($C_1$-$C_6$)-haloalkoxy, ($C_3$-$C_8$)-cycloalkylcarbonyl, ($C_3$-$C_8$)-cycloalkoxycarbonyl, ($C_3$-$C_8$)-cycloalkyl-($C_1$-$C_6$)-alkylcarbonyl, ($C_3$-$C_8$)-cycloalkyl-($C_1$-$C_6$)-haloalkylcarbonyl, ($C_3$-$C_8$)-cycloalkyl-($C_1$-$C_6$)-alkoxycarbonyl, ($C_3$-$C_8$)-cycloalkyl-($C_1$-$C_6$)-haloalkoxycarbonyl, ($C_3$-$C_8$)-cycloalkylcarbonyloxy, ($C_3$-$C_8$)-cycloalkoxycarbonyloxy, ($C_3$-$C_8$)-cycloalkyl-($C_1$-$C_6$)-alkylcarbonyloxy, ($C_3$-$C_8$)-cycloalkyl-($C_1$-$C_6$)-haloalkylcarbonyloxy, ($C_3$-$C_8$)-cycloalkyl-($C_1$-$C_6$)-alkoxycarbonyloxy, ($C_3$-$C_8$)-cycloalkyl-($C_1$-$C_6$)-haloalkoxycarbonyloxy;

($C_3$-$C_8$)-cycloalkenyl, ($C_3$-$C_8$)-cycloalkenyloxy, ($C_3$-$C_8$)-cycloalkenyl-($C_1$-$C_6$)-alkyl, ($C_3$-$C_8$)-cycloalkenyl-($C_1$-$C_6$)-haloalkyl, ($C_3$-$C_8$)-cycloalkenyl-($C_1$-$C_6$)-alkoxy, ($C_3$-$C_8$)-cycloalkenyl-($C_1$-$C_6$)-haloalkoxy, ($C_3$-$C_8$)-cycloalkenylcarbonyl, ($C_3$-$C_8$)-cycloalkenyloxycarbonyl, ($C_3$-$C_8$)-cycloalkenyl-($C_1$-$C_6$)-alkylcarbonyl, ($C_3$-$C_8$)-cycloalkenyl-($C_1$-$C_6$)-haloalkylcarbonyl, ($C_3$-$C_8$)-cycloalkenyl-($C_1$-$C_6$)-alkoxycarbonyl, ($C_3$-$C_8$)-cycloalkenyl-($C_1$-$C_6$)-haloalkoxycarbonyl, ($C_3$-$C_8$)-cycloalkenylcarbonyloxy, ($C_3$-$C_8$)-cycloalkenyloxycarbonyloxy, ($C_3$-$C_8$)-cycloalkenyl-($C_1$-$C_6$)-alkylcarbonyloxy, ($C_3$-$C_8$)-cycloalkenyl-($C_1$-$C_6$)-haloalkylcarbonyloxy, ($C_3$-$C_8$)-cycloalkenyl-($C_1$-$C_6$)-alkoxycarbonyloxy, ($C_3$-$C_8$)-cycloalkenyl-($C_1$-$C_6$)-haloalkoxycarbonyloxy;

hydroxy-($C_1$-$C_6$)-alkyl, hydroxy-($C_1$-$C_6$)-alkoxy, cyano-($C_1$-$C_6$)-alkoxy, cyano-($C_1$-$C_6$)-alkyl;

($C_1$-$C_6$)-alkylsulfonyl, ($C_1$-$C_6$)-alkylthio, ($C_1$-$C_6$)-alkylsulfinyl, ($C_1$-$C_6$)-haloalkylsulfonyl, ($C_1$-$C_6$)-haloalkylthio, ($C_1$-$C_6$)-haloalkylsulfinyl, ($C_1$-$C_6$)-alkylsulfonyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl, ($C_1$-$C_6$)-alkylsulfonyloxy, ($C_1$-$C_6$)-haloalkylsulfonyloxy, ($C_1$-$C_6$)-alkylthiocarbonyl, ($C_1$-$C_6$)-haloalkylthiocarbonyl, ($C_1$-$C_6$)-alkylthiocarbonyloxy, ($C_1$-$C_6$)-haloalkylthiocarbonyloxy, ($C_1$-$C_6$)-alkylthio-($C_1$-$C_6$)-alkyl, ($C_1$-$C_6$)-alkylthio-($C_1$-$C_6$)-alkoxy, ($C_1$-$C_6$)-alkylthio-($C_1$-$C_6$)-alkylcarbonyl, ($C_1$-$C_6$)-alkylthio-($C_1$-$C_6$)-alkylcarbonyloxy; ($C_4$-$C_{14}$)-arylsulfonyl, ($C_6$-$C_{14}$)-arylthio, ($C_6$-$C_{14}$)-arylsulfinyl, ($C_3$-$C_8$)-cycloalkylthio, ($C_3$-$C_8$)-alkenylthio, ($C_3$-$C_6$)-cycloalkenylthio, ($C_3$-$C_6$)-alkynylthio; and $R^{2a}$ and $R^{2b}$, each independently of one another, are selected from the group consisting of hydrogen, halogen, hydroxy, cyano, nitro, C(O)OH, C(O)NH$_2$;

($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-haloalkylcarbonyloxy, ($C_1$-$C_6$)-alkylcarbonyl-($C_1$-$C_4$)-alkyl;

($C_1$-$C_6$)-alkoxy, ($C_1$-$C_6$)-haloalkoxy, ($C_1$-$C_6$)-alkoxycarbonyl, ($C_1$-$C_6$)-haloalkoxycarbonyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;

($C_2$-$C_6$)-alkenyl, ($C_2$-$C_6$)-haloalkenyl, ($C_2$-$C_6$)-alkenylcarbonyl, ($C_2$-$C_6$)-haloalkenylcarbonyl, ($C_2$-$C_6$)-alkenyloxy, ($C_2$-$C_6$)-haloalkenyloxy, ($C_2$-$C_6$)-alkenyloxycarbonyl, ($C_2$-$C_6$)-haloalkenyloxycarbonyl;

($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl;

tri-($C_1$-$C_6$)-alkylsilyl-($C_2$-$C_6$)-alkynyl, di-($C_1$-$C_6$)-alkylsilyl-($C_2$-$C_6$)-alkynyl, mono-($C_1$-$C_6$)-alkylsilyl-($C_2$-$C_6$)-alkynyl; phenylsilyl-($C_2$-$C_6$)-alkynyl;

($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl, each of which may be substituted at the aryl moiety by halogen, ($C_1$-$C_6$)-alkyl and/or ($C_1$-$C_6$)-haloalkyl;

($C_6$-$C_{14}$)-aryl-($C_1$-$C_6$)-alkyl, ($C_6$-$C_{14}$)-aryl-($C_1$-$C_6$)-alkoxy, ($C_6$-$C_{14}$)-aryl-($C_1$-$C_6$)-alkyl-carbonyl, ($C_6$-$C_{14}$)-aryl-($C_1$-$C_6$)-alkyl-carbonyloxy, ($C_6$-$C_{14}$)-aryl-($C_1$-$C_6$)-alkoxycarbonyl, ($C_6$-$C_{14}$)-aryl-($C_1$-$C_6$)-alkoxycarbonyloxy;

aminocarbonyl-($C_1$-$C_6$)-alkyl, di-($C_1$-$C_6$)-alkylaminocarbonyl-($C_1$-$C_6$)-alkyl;

N—(($C_1$-$C_6$)-haloalkanoyl)-amino-carbonyl, mono-(($C_6$-$C_{14}$)-aryl)-amino-carbonyl, di-(($C_6$-$C_{14}$)-aryl)-amino-carbonyl;

($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy;

($C_3$-$C_8$)-cycloalkyl which may optionally be substituted at the cycloalkyl radical by ($C_1$-$C_6$)-alkyl and/or halogen; ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-haloalkyl, ($C_3$-$C_8$)-cycloalkyl-($C_1$-$C_6$)-alkoxy, ($C_3$-$C_8$)-cycloalkyl-($C_1$-$C_6$)-haloalkoxy, ($C_3$-$C_8$)-cycloalkylcarbonyl, ($C_3$-$C_8$)-cycloalkoxycarbonyl, ($C_3$-$C_8$)-cycloalkyl-($C_1$-$C_6$)-alkylcarbonyl, ($C_3$-$C_8$)-cycloalkyl-($C_1$-$C_6$)-haloalkylcarbonyl, ($C_3$-$C_8$)-cycloalkyl-($C_1$-$C_6$)-alkoxycarbonyl, ($C_3$-$C_8$)-cycloalkyl-($C_1$-$C_6$)-haloalkoxycarbonyl, ($C_3$-$C_8$)-cycloalkylcarbonyloxy, ($C_3$-$C_8$)-cycloalkoxycarbonyloxy, ($C_3$-$C_8$)-cycloalkyl-($C_1$-$C_6$)-alkylcarbonyloxy, ($C_3$-$C_8$)-cycloalkyl-($C_1$-$C_6$)-haloalkylcarbonyloxy, ($C_3$-$C_8$)-cycloalkyl-($C_1$-$C_6$)-alkoxycarbonyloxy, ($C_3$-$C_8$)-cycloalkyl-($C_1$-$C_6$)-haloalkoxycarbonyloxy;

($C_3$-$C_8$)-cycloalkenyl, ($C_3$-$C_8$)-cycloalkenyloxy, ($C_3$-$C_8$)-cycloalkenyl-($C_1$-$C_6$)-alkyl, ($C_3$-$C_8$)-cycloalkenyl-($C_1$-$C_6$)-haloalkyl, ($C_3$-$C_8$)-cycloalkenyl-($C_1$-$C_6$)-alkoxy, ($C_3$-$C_8$)-cycloalkenyl-($C_1$-$C_6$)-haloalkoxy, ($C_3$-$C_8$)-cycloalkenylcarbonyl, ($C_3$-$C_8$)-cycloalkenyloxycarbonyl, ($C_3$-$C_8$)-cycloalkenyl-($C_1$-$C_6$)-alkylcarbonyl, ($C_3$-$C_8$)-cycloalkenyl-($C_1$-$C_6$)-haloalkylcarbonyl, ($C_3$-$C_8$)-cycloalkenyl-($C_1$-$C_6$)-alkoxycarbonyl, ($C_3$-$C_8$)-cycloalkenyl-($C_1$-$C_6$)-haloalkoxycarbonyl, ($C_3$-$C_8$)-cycloalkenylcarbonyloxy, ($C_3$-$C_8$)-cycloalkenyloxycarbonyloxy, ($C_3$-$C_8$)-cycloalkenyl- ($C_1$-$C_6$)-alkylcarbonyloxy, ($C_3$-$C_8$)-cycloalkenyl-($C_1$-$C_6$)-haloalkylcarbonyloxy, ($C_3$-$C_8$)-cycloalkenyl-($C_1$-$C_6$)-alkoxycarbonyloxy, ($C_3$-$C_8$)-cycloalkenyl-($C_1$-$C_6$)-haloalkoxycarbonyloxy; hydroxy-($C_1$-$C_6$)-alkyl, hydroxy-($C_1$-$C_6$)-alkoxy, cyano-($C_1$-$C_6$)-alkoxy, cyano-($C_1$-$C_6$)-alkyl; ($C_1$-$C_6$)-alkylsulfonyl, ($C_1$-$C_6$)-alkylthio, ($C_1$-$C_6$)-alkylsulfinyl, ($C_1$-$C_6$)-haloalkylsulfonyl, ($C_1$-$C_6$)-haloalkylthio, ($C_1$-$C_6$)-haloalkylsulfinyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl, ($C_1$-$C_6$)-alkylsulfonyloxy, ($C_1$-$C_6$)-haloalkylsulfonyloxy, ($C_1$-$C_6$)-alkylthiocarbonyl, ($C_1$-$C_6$)-haloalkylthiocarbonyl, ($C_1$-$C_6$)-alkylthiocarbonyloxy, ($C_1$-$C_6$)-haloalkylthiocarbonyloxy, ($C_1$-$C_6$)-alkylthio-($C_1$-$C_6$)-alkyl, ($C_1$-$C_6$)-alkylthio-($C_1$-$C_6$)-alkoxy, ($C_1$-$C_6$)-alkylthio-($C_1$-$C_6$)-alkylcarbonyl, ($C_1$-$C_6$)-alkylthio-($C_1$-$C_6$)-alkylcarbonyloxy; ($C_4$-$C_{14}$)-arylsulfonyl, ($C_6$-$C_{14}$)-arylthio, ($C_6$-$C_{14}$)-arylsulfinyl, ($C_3$-$C_8$)-cycloalkylthio, ($C_3$-$C_8$)-alkenylthio, ($C_3$-$C_8$)-cycloalkenylthio, ($C_3$-$C_6$)-alkynylthio; and $R^3$ is selected from the group consisting of
hydrogen, cyano, C(O)OH, C(O)NH$_2$;
($C_1$-$C_6$)-alkyl and ($C_1$-$C_6$)-haloalkyl;
($C_1$-$C_6$)-alkoxycarbonyl; and $R^4$ and $R^5$, each independently of one another, are selected from the group consisting of hydrogen, ($C_1$-$C_6$)-alkyl, ($C_1$-$C_6$)-haloalkyl, hydroxy, ($C_1$-$C_6$)-alkoxy and ($C_1$-$C_6$)-haloalkoxy; or the radicals $R^4$ and $R^5$ together with the carbon atom to which they are attached form a three-to seven-membered ring; and $R^6$ and $R^7$, each independently of one another, are selected from the group consisting of hydrogen, ($C_1$-$C_6$)-alkyl, ($C_1$-$C_6$)-haloalkyl, ($C_1$-$C_6$)-alkoxy, ($C_1$-$C_6$)-haloalkoxy, ($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl; or the radicals $R^6$ and $R^7$ together form a ($C_1$-$C_7$)-alkylene group which may contain one or more oxygen and/or sulfur atoms, where the ($C_1$-$C_7$)-alkylene group may be mono- or polysubstituted by halogen and the halogen substituents in question may be identical or different, and n is the running number 0, 1 or 2 and $R^8$, $R^9$, $R^{10}$ and $R^{11}$, each independently of one another, are selected from the group consisting of hydrogen, halogen, cyano, C(O)OH, C(O)NH$_2$, ($C_1$-$C_6$)-alkyl, ($C_1$-$C_6$)-alkylcarbonyl, ($C_1$-$C_6$)-alkyloxycarbonyl, ($C_1$-$C_6$)-alkylaminocarbonyl, ($C_1$-$C_6$)-di-alkylaminocarbonyl, ($C_1$-$C_6$)-haloalkyl, ($C_1$-$C_6$)-alkoxy, ($C_1$-$C_6$)-haloalkoxy, ($C_2$-$C_6$)-alkenyl, ($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl and ($C_2$-$C_6$)-haloalkynyloxycarbonyl and nitro;

X is a bond, CH$_2$, O, S, carbonyl, NH, CR$^{12}$R$^{13}$ and NR$^{14}$ or CH$_2$O, CH$_2$S, where in the two last-mentioned groups the carbon atom is attached to the aromatic moiety and the heteroatom O or S is attached to the partially hydrogenated moiety of the amine; and $R^{12}$ and $R^{13}$, each independently of one another, are selected from the group consisting of hydrogen, ($C_1$-$C_6$)-alkyl and ($C_1$-$C_6$)-haloalkyl; and $R^{14}$ is selected from the group consisting of hydrogen, ($C_1$-$C_6$)-alkyl, ($C_1$-$C_6$)-haloalkyl.

DETAILED DESCRIPTION OF A PREFERRED EMBODIMENT

In addition to having a good activity profile and good crop plant compatibility, the compounds of the formula (I) are distinguished by their cost-efficient preparation, since the substances according to the invention can be prepared from cheap and easily accessible precursors by cost-effective processes, and the use of expensive intermediates which are difficult to obtain can therefore be dispensed with.

Hereinbelow, preferred, particularly preferred and very particularly preferred meanings are described for each of the individual substituents.

A first embodiment of the present invention comprises compounds of the general formula (I) in which $R^1$ is preferably selected from the group consisting of
hydrogen, halogen, cyano, NO$_2$, ($C_1$-$C_6$)-alkyl, ($C_1$-$C_6$)-haloalkyl, ($C_1$-$C_6$)-alkoxy, ($C_1$-$C_6$)-haloalkoxy, ($C_1$-$C_6$)-alkylthio, ($C_1$-$C_6$)-alkyl sulfoxide, ($C_1$-$C_6$)-alkylsulfonyl, ($C_1$-$C_6$)-haloalkylsulfonyl, ($C_1$-$C_6$)-alkoxycarbonyl, amino-carbonyl, mono-(($C_1$-$C_6$)-alkyl)-amino-carbonyl, di-(($C_1$-$C_6$)-alkyl)-amino-carbonyl, ($C_6$-$C_{14}$)-aryl, ($C_6$-$C_{14}$)-aryl-haloalkyl, ($C_1$-$C_6$)-aryloxy, ($C_6$-$C_{14}$)-haloaryl-($C_1$-$C_6$)-alkyl, ($C_2$-$C_6$)-alkynyl-($C_1$-$C_6$)-alkoxy, ($C_2$-$C_6$)-alkynyl-($C_1$-$C_6$)-alkyl-($C_1$-$C_6$)-alkoxy and ($C_1$-$C_6$)-alkyl-($C_2$-$C_6$)-alkynyl-($C_1$-$C_6$)-alkoxy;

$R^1$ is particularly preferably selected from the group consisting of
cyano (CN), NO$_2$, ($C_1$-$C_3$)-alkyl, ($C_1$-$C_6$)-haloalkyl, ($C_1$-$C_6$)-alkoxy, ($C_1$-$C_6$)-haloalkoxy, ($C_1$-$C_6$)-alkylthio, ($C_1$-$C_6$)-alkyl sulfoxide, ($C_1$-$C_6$)-alkylsulfonyl, ($C_1$-$C_6$)-haloalkylsulfonyl, ($C_1$-$C_6$)-alkoxy-carbonyl, amino-carbonyl, mono-(($C_1$-$C_6$)-alkyl)-amino-carbonyl, di-(($C_1$-$C_6$)-alkyl)-amino-carbonyl, ($C_6$-$C_{14}$)-aryl, ($C_6$-$C_{14}$)-aryl-haloalkyl, ($C_1$-$C_6$)-aryloxy, ($C_6$-$C_{14}$)-haloaryl-($C_1$-$C_6$)-alkyl, ($C_2$-$C_6$)-alkynyl-($C_1$-$C_6$)-alkoxy, ($C_2$-$C_6$)-alkynyl-($C_1$-$C_6$)-alkyl-($C_1$-$C_6$)-alkoxy and ($C_1$-$C_6$)-alkyl-($C_2$-$C_6$)-alkynyl-($C_1$-$C_6$)-alkoxy;

$R^1$ is very particularly preferably selected from the group consisting of CN, NO$_2$, CH$_3$, CH$_2$CH$_3$, CH(CH$_3$)$_2$, OCH$_3$, CF$_3$, CF$_2$Cl, CF$_2$H, CFHCH$_3$, CF$_2$CF$_3$, OCH$_3$, OCH$_2$CH$_3$, OCH$_2$CF$_3$, SCH$_3$, SOCH$_3$, SO$_2$CH$_3$, SO$_2$CH$_2$CH$_3$, SO$_2$CF$_3$, COOCH$_3$, COOCH$_2$CH$_3$, CONH$_2$, CONHCH$_3$, CON(CH$_3$)$_2$, C$_6$H$_5$—, CHF—C$_6$H$_5$, OC$_6$H$_5$, CH$_2$C$_6$H$_4$-4-Cl, OCH$_2$C≡CH, OCH(CH$_3$)C≡CH, OCH$_2$C≡CCH$_3$; and in which $R^1$ is most preferably SO$_2$CH$_3$.

A second embodiment of the present invention comprises compounds of the general formula (I) in which $R^{2a}$ and $R^{2b}$, each independently of one another, are preferably selected from the group consisting of hydrogen, CN, hydroxy, ($C_1$-$C_6$)-alkyl, ($C_1$-$C_6$)-haloalkyl, ($C_1$-$C_6$)-cycloalkyl, ($C_1$-$C_6$)-alkoxy, aminocarbonyl, hydroxycarbonyl, ($C_1$-$C_6$)-alkoxycarbonyl, ($C_1$-$C_6$)-alkylsulfonyl, mono-(($C_1$-$C_6$)-alkyl)-amino-carbonyl, di-(($C_1$-$C_6$)-alkyl)-amino-carbonyl, mono-(($C_6$-$C_{14}$)-aryl)-amino-carbonyl, mono-(($C_2$-$C_6$)-alkylene)-amino-carbonyl, mono-(($C_6$-$C_{14}$)-aryl-($C_1$-$C_6$)-alkyl)-amino-carbonyl, ($C_1$-$C_6$)-alkoxy-($C_1$-$C_6$)-alkoxy-carbonyl and di-(($C_1$-$C_6$)-alkyl)-amino-($C_1$-$C_6$)-alkoxycarbonyl;

$R^{2a}$ and $R^{2b}$, each independently of one another, are particularly preferably selected from the group consisting of hydrogen, CN, hydroxy (OH), $(C_1-C_6)$-alkyl, $(C_1-C_6)$-haloalkyl, $(C_1-C_6)$-cycloalkyl, $(C_1-C_6)$-alkoxy, aminocarbonyl, hydroxycarbonyl COOH, $(C_1-C_6)$-alkoxycarbonyl, $(C_1-C_6)$-alkylsulfonyl, mono-$((C_1-C_6)$-alkyl)-amino-carbonyl, di-$((C_1-C_6)$-alkyl)-amino-carbonyl, mono-$((C_6-C_{14})$-aryl)-amino-carbonyl, mono-$((C_2-C_6)$-alkylene)-amino-carbonyl, mono-$((C_6-C_{14})$-aryl-$(C_1-C_6)$-alkyl)-amino-carbonyl, $(C_1-C_6)$-alkoxy-$(C_1-C_6)$-alkoxy-carbonyl and di-$((C_1-C_6)$-alkyl)-amino-$(C_1-C_6)$-alkoxycarbonyl; and in which $R^{2a}$ and $R^{2b}$, each independently of one another, are very particularly preferably selected from the group consisting of hydrogen, CN, hydroxy (OH), $CH_3$, $CH_2CH_3$, $CH(CH_3)_2$, $C(CH_3)_3$, $CF_3$, $CF_2H$, $CF_2Cl$, cyclopropyl, $OCH_3$, $CONH_2$, COOH, $COOCH_3$, $COOCH_2CH_3$, $SO_2CH_3$, $CONHCH_3$, CONHcyprop, $CON(CH_3)_2$, $CON(CH_2CH_3)_2$, $CONHC_6H_5$, $CONHCH_2CH=CH_2$, $CONHCH_2C_6H_5$, $COOCH_2CH_2OCH_3$, $COOCH_2CH_2N(CH_3)_2$ $R^{2a}$ and $R^{2b}$, each independently of one another, are most particularly preferably selected from the group consisting of compounds of the general formula (I) in which $R^{2a}$ is selected from the group consisting of hydrogen, $CH_3$, $CH_2CH_3$ and $CF_3$, and $R^{2b}$ is selected from the group consisting of hydrogen and $CH_3$.

A third embodiment of the present invention comprises compounds of the general formula (I) in which $R^3$ is preferably selected from the group consisting of hydrogen, $(C_1-C_6)$-alkyl, $(C_1-C_6)$-alkoxy, $(C_1-C_6)$-alkoxy-$(C_1-C_6)$-alkyl, $(C_1-C_6)$-alkoxy-carbonyl, aminocarbonyl, $(C_6-C_{14})$-aryl;

$R^3$ is particularly preferably selected from the group consisting of hydrogen, $CH_3$, $CH_2CH_2OCH_3$, $COOCH_3$, $CONH_2$ and $C_6H_5$; and $R^3$ is very particularly preferably selected from the group consisting of hydrogen, $CH_3$, $CH_2CH_2OCH_3$; and in which $R^3$ is most preferably hydrogen.

A fourth embodiment of the present invention comprises compounds of the general formula (I) in which $R^4$ and $R^5$, each independently of one another, are preferably selected from the group consisting of hydrogen, cyano, hydroxy, $(C_1-C_6)$-alkyl, $(C_1-C_6)$-alkylphenyl and $(C_1-C_6)$-alkoxy;

$R^4$ and $R^5$, each independently of one another, are particularly preferably selected from the group consisting of hydrogen, cyano, hydroxy, $(C_1-C_6)$-alkyl and $(C_1-C_6)$-alkoxy;

$R^4$ and $R^5$, each independently of one another, are particularly preferably selected from the group consisting of hydrogen, cyano, hydroxy, $CH_3$, $CH_2CH_3$, $CH_2C_6H_5$ and $OCH_3$; and in which $R^4$ and $R^5$, each independently of one another, are most preferably methyl or hydrogen.

In this fourth embodiment, it is therefore especially preferred if at least one of the radicals $R^4$ and $R^5$ is hydrogen. It is furthermore preferred for at least one of the radicals $R^4$ and $R^5$ to be hydrogen and for the other radical $R^4$ and $R^5$ not to be hydrogen, in particular $(C_1-C_6)$-alkyl, preferably methyl $(CH_3)$.

A fifth embodiment of the present invention comprises compounds of the general formula (I) in which $R^4$ and $R^5$ are preferably a $(C_1-C_7)$-alkylene group and together with the carbon atom to which they are attached form a three- to seven-membered ring;

$R^4$ and $R^5$ are particularly preferably a $(C_1-C_3)$-alkylene group and together with the carbon atom to which they are attached form a three- or four-membered ring; and in which $R^4$ and $R^5$ are very particularly preferably the alkylene group ($—CH_2—CH_2—$) and together with the carbon atom to which they are attached form a three-membered ring.

A sixth embodiment of the present invention comprises compounds of the general formula (I) in which $R^6$ and $R^7$, independently of one another, are preferably selected from the group consisting of hydrogen, $(C_1-C_6)$-alkyl and $(C_6-C_{14})$-aryl;

$R^6$ and $R^7$, independently of one another, are particularly preferably selected from the group consisting of hydrogen, methyl and phenyl; and in which $R^6$ and $R^7$ are very particularly preferably hydrogen.

A seventh embodiment of the present invention comprises compounds of the general formula (I) in which $R^8$ is preferably selected from the group consisting of hydrogen, halogen, $(C_1-C_6)$-alkyl, $(C_1-C_6)$-alkoxy and di-$(C_1-C_6)$-alkylamino;

$R^8$ is particularly preferably selected from the group consisting of hydrogen, halogen, $(C_1-C_6)$-alkyl, $(C_1-C_6)$-alkoxy and di-$(C_1-C_6)$-alkylamino; and $R^8$ is very particularly preferably selected from the group consisting of hydrogen, fluorine, chlorine, $CH_3$, $OCH_3$ and $N(CH_3)_2$; and in which $R^8$ is most preferably hydrogen.

An eighth embodiment of the present invention comprises compounds of the general formula (I) in which $R^9$ is preferably selected from the group consisting of hydrogen, halogen, $(C_1-C_6)$-alkyl, $(C_1-C_6)$-alkoxy;

$R^9$ is particularly preferably selected from the group consisting of hydrogen, chlorine, fluorine, $(C_1-C_6)$-alkyl and $(C_1-C_6)$-alkoxy; and $R^9$ is very particularly preferably selected from the group consisting of hydrogen, fluorine, chlorine, methyl and methoxy; and in which $R^9$ is most preferably hydrogen.

A ninth embodiment of the present invention comprises compounds of the general formula (I) in which $R^{10}$ is preferably selected from the group consisting of hydrogen, halogen, cyano, aminocarbonyl, hydroxycarbonyl, $(C_1-C_6)$-alkyl, $(C_1-C_6)$-alkoxy, $(C_2-C_6)$-alkenyl, $(C_2-C_6)$-alkynyl and $(C_1-C_6)$-alkyl-$(C_2-C_6)$-alkynyl;

$R^{10}$ is particularly preferably selected from the group consisting of hydrogen, fluorine, chlorine, bromine, cyano, $CONH_2$, COOH, methyl ($CH_3$), ethyl ($CH_2CH_3$), methoxy ($OCH_3$), $CH=CH_2$, $C\equiv CH$ and $C\equiv CCH_3$; and in which $R^{10}$ is very particularly preferably hydrogen or methyl.

A tenth embodiment of the present invention comprises compounds of the general formula (I) in which $R^{11}$ is preferably selected from the group consisting of hydrogen and $(C_1-C_6)$-alkyl;

$R^{11}$ is particularly preferably selected from the group consisting of hydrogen and methyl; and $R^{11}$ is very particularly preferably hydrogen.

An eleventh embodiment of the present invention comprises compounds of the general formula (I) in which X is preferably selected from the group consisting of O, S, carbonyl, $CH_2$, NH, CH—$(C_1-C_6)$-alkyl, di-$(C_1-C_6)$-alkyl-alkylene, O—$(C_1-C_7)$-alkylene, S—$(C_1-C_7)$-alkylene, $(C_1-C_6)$-alkylamino, or in which X is a chemical bond;

X is particularly preferably selected from the group consisting of O, S, carbonyl, $CH_2$, NH, $CHCH_3$, $NCH_3$, $C(CH_3)_2$, $OCH_2$, $SCH_2$, or in which X is a chemical bond; and X is very particularly preferably selected from the group consisting of O and S, or in which X is a chemical bond.

In the context of the present invention, it is possible to combine the specific preferred, particularly preferred and very particularly preferred meanings of the substituents $R^1$ to $R^{11}$ and X with one another as desired. This means that the present invention encompasses compounds of the general formula (I) in which, for example, the substituent $R^1$ has a preferred meaning and the substituents $R^2$ to $R^{14}$ have the general meaning or else the substituent $R^2$ has a preferred meaning, the substituent $R^3$ has a particularly preferred or a very particularly preferred meaning and the remaining substituents have a general meaning.

Three of these combinations of the definitions given above for the substituents $R^1$ to $R^{11}$ and X are disclosed and illustrated in an exemplary manner below, as further embodiments:
- combination of the definitions referred to above as being particularly preferred for the substituents $R^1$ to $R^{11}$ and X (twelfth embodiment),
- combination of the definitions referred to above as being very particularly preferred for the substituents $R^1$ to $R^{11}$ and X (thirteenth embodiment), and
- combination of the definition referred to above as being very particularly preferred for the substituent $R^1$ with the definitions referred to above as being very particularly preferred for the substituents R2 to R11 and X (fourteenth embodiment)

A twelfth embodiment of the present invention comprises compounds of the general formula (I) in which
$R^1$ is selected from the group consisting of
  cyano (CN), $NO_2$, $(C_1-C_3)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-alkyl sulfoxide, $(C_1-C_6)$-alkylsulfonyl, $(C_1-C_6)$-haloalkylsulfonyl, $(C_1-C_6)$-alkoxy-carbonyl, amino-carbonyl, mono-$((C_1-C_6)$-alkyl)-amino-carbonyl, di-$((C_1-C_6)$-alkyl)-amino-carbonyl, $(C_6-C_{14})$-aryl, $(C_6-C_{14})$-aryl-haloalkyl, $(C_1-C_6)$-aryloxy, $(C_6-C_{14})$-haloaryl-$(C_1-C_6)$-alkyl, $(C_2-C_6)$-alkynyl-$(C_1-C_6)$-alkoxy, $(C_2-C_6)$-alkynyl-$(C_1-C_6)$-alkyl-$(C_1-C_6)$-alkoxy and $(C_1-C_6)$-alkyl-$(C_2-C_6)$-alkynyl-$(C_1-C_6)$-alkoxy;
$R^{2a}$ and $R^{2b}$, each independently of one another, are selected from the group consisting of hydrogen, CN, hydroxy (OH), $(C_1-C_6)$-alkyl, $(C_1-C_6)$-haloalkyl, $(C_1-C_6)$-cycloalkyl, $(C_1-C_6)$-alkoxy, aminocarbonyl, hydroxycarbonyl COOH, $(C_1-C_6)$-alkoxycarbonyl, $(C_1-C_6)$-alkylsulfonyl, mono-$((C_1-C_6)$-alkyl)-amino-carbonyl, di-$((C_1-C_6)$-alkyl)-amino-carbonyl, mono-$((C_6-C_{14})$-aryl)-amino-carbonyl, mono-$((C_2-C_6)$-alkylene)-amino-carbonyl, mono-$((C_6-C_{14})$-aryl-$(C_1-C_6)$-alkyl)-amino-carbonyl, $(C_1-C_6)$-alkoxy-$(C_1-C_6)$-alkoxy-carbonyl and di-$((C_1-C_6)$-alkyl)-amino-$(C_1-C_6)$-alkoxycarbonyl;
$R^3$ is selected from the group consisting of
  hydrogen, $CH_3$, $CH_2CH_2OCH_3$, $COOCH_3$, $CONH_2$ and $C_6H_5$;
$R^4$ and $R^5$, each independently of one another, are selected from the group consisting of hydrogen, cyano, hydroxy, $(C_1-C_6)$-alkyl and $(C_1-C_6)$-alkoxy; or alternatively
$R^4$ and $R^5$ are a $(C_1-C_3)$-alkylene group and together with the carbon atom to which they are attached form a three- or four-membered ring;
$R^6$ and $R^7$, independently of one another, are selected from the group consisting of hydrogen, methyl and phenyl;
$R^8$ is selected from the group consisting of hydrogen, halogen, $(C_1-C_6)$-alkyl, $(C_1-C_6)$-alkoxy and di-$(C_1-C_6)$-alkylamino;
$R^9$ is selected from the group consisting of hydrogen, chlorine, fluorine, $(C_1-C_6)$-alkyl and $(C_1-C_6)$-alkoxy;
$R^{10}$ is selected from the group consisting of hydrogen, fluorine, chlorine, bromine, cyano, $CONH_2$, COOH, methyl ($CH_3$), ethyl ($CH_2CH_3$), methoxy ($OCH_3$), $CH=CH_2$, $C\equiv CH$ and $C\equiv CCH_3$;
$R^{11}$ is selected from the group consisting of hydrogen and methyl; and in which
X is selected from the group consisting of
  O, S, carbonyl, $CH_2$, NH, $CHCH_3$, $NCH_3$, $C(CH_3)_2$, $OCH_2$, $SCH_2$, or in which X is a chemical bond.

A thirteenth embodiment of the present invention comprises compounds of the general formula (I) in which
$R^1$ is selected from the group consisting of
  CN, $NO_2$, $CH_3$, $CH_2CH_3$, $CH(CH_3)_2$, $OCH_3$, $CF_3$, $CF_2Cl$, $CF_2H$, $CFHCH_3$, $CF_2CF_3$, $OCH_3$, $OCH_2CH_3$, $OCH_2CF_3$, $SCH_3$, $SO_2CH_3$, $SO_2CH_3$, $SO_2CH_2CH_3$, $SO_2CF_3$, $COOCH_3$, $COOCH_2CH_3$, $CONH_2$, $CONHCH_3$, $CON(CH_3)_2$, $C_6H_5-$, $CHF-C_6H_5$, $OC_6H_5$, $CH_2C_6H_4$-4-Cl, $OCH_2C=CH$, $OCH(CH_3)C=CH$, $OCH_2C\equiv CCH_3$;
$R^{2a}$ and $R^{2b}$, each independently of one another, are selected from the group consisting of
  hydrogen, CN, hydroxy (OH), $CH_3$, $CH_2CH_3$, $CH(CH_3)_2$, $C(CH_3)_3$, $CF_3$, $CF_2H$, $CF_2Cl$, cyclopropyl, $OCH_3$, $CONH_2$, COOH, $COOCH_3$, $COOCH_2CH_3$, $SO_2CH_3$, $CONHCH_3$, CONHcyprop, $CON(CH_3)_2$, $CON(CH_2CH_3)_2$, $CONHC_6H_5$, $CONHCH_2CH=CH_2$, $CONHCH_2C_6H_5$, $COOCH_2CH_2OCH_3$, $COOCH_2CH_2N(CH_3)_2$;
$R^3$ is selected from the group consisting of
  hydrogen, $CH_3$, $CH_2CH_2OCH_3$; and in which
$R^4$ and $R^5$, each independently of one another, are selected from the group consisting of hydrogen, cyano, hydroxy, $CH_3$, $CH_2CH_3$, $CH_2C_6H_5$ and $OCH_3$; or alternatively
$R^4$ and $R^5$ are the alkylene group ($-CH_2-CH_2-$) and together with the carbon atom to which they are attached form a three-membered ring;
$R^6$ and $R^7$, independently of one another, are selected from the group consisting of hydrogen, methyl and phenyl;
$R^8$ is selected from the group consisting of hydrogen, fluorine, chlorine, $CH_3$, $OCH_3$ and $N(CH_3)_2$;
$R^9$ is selected from the group consisting of hydrogen, fluorine, chlorine, methyl and methoxy;
$R^{10}$ is hydrogen or methyl;
$R^{11}$ is hydrogen; and in which
X is selected from the group consisting of
  O and S, or in which X is a chemical bond.

A fourteenth embodiment of the present invention comprises compounds of the general formula (I) in which
$R^1$ is selected from the group consisting of
  CN, $NO_2$, $CH_3$, $CH_2CH_3$, $CH(CH_3)_2$, $OCH_3$, $CF_3$, $CF_2Cl$, $CF_2H$, $CFHCH_3$, $CF_2CF_3$, $OCH_3$, $OCH_2CH_3$, $OCH_2CF_3$, $SCH_3$, $SOCH_3$, $SO_2CH_3$, $SO_2CH_2CH_3$, $SO_2CF_3$, $COOCH_3$, $COOCH_2CH_3$, $CONH_2$, $CONHCH_3$, $CON(CH_3)_2$, $C_6H_5-$, $CHF-C_6H_5$, $OC_6H_5$, $CH_2C_6H_4$-4-Cl, $OCH_2C=CH$, $OCH(CH_3)C=CH$, $OCH_2C\equiv CCH_3$;
$R^3$ is from the group consisting of
  hydrogen, $CH_3$, $CH_2CH_2OCH_3$, $COOCH_3$, $CONH_2$ and $C_6H_5$;
$R^4$ and $R^5$, each independently of one another, are selected from the group consisting of hydrogen, cyano, hydroxy, $(C_1-C_6)$-alkyl and $(C_1-C_6)$-alkoxy; or alternatively
$R^4$ and $R^5$ are a $(C_1-C_3)$-alkylene group and together with the carbon atom to which they are attached form a three- or four-membered ring;
$R^6$ and $R^7$, independently of one another, are selected from the group consisting of hydrogen, methyl and phenyl;

$R^8$ is selected from the group consisting of hydrogen, halogen, $(C_1-C_6)$-alkyl, $(C_1-C_6)$-alkoxy and di-$(C_1-C_6)$-alkylamino;

$R^9$ is selected from the group consisting of hydrogen, chlorine, fluorine, $(C_1-C_6)$-alkyl and $(C_1-C_6)$-alkoxy;

$R^{10}$ is selected from the group consisting of hydrogen, fluorine, chlorine, bromine, cyano, $CONH_2$, COOH, methyl ($CH_3$), ethyl ($CH_2CH_3$), methoxy ($OCH_3$), $CH=CH_2$, $C\equiv CH$ and $C\equiv CCH_3$;

$R^{11}$ is selected from the group consisting of hydrogen and methyl; and in which X is selected from the group consisting of
O, S, carbonyl, $CH_2$, NH, $CHCH_3$, $NCH_3$, $C(CH_3)_2$, $OCH_2$, $SCH_2$, or in which X is a chemical bond.

In the context of the present invention, the compounds of the general formula (I) also comprise compounds quaternized at a nitrogen atom by a) protonation, b) alkylation or c) oxidation. In this respect, particular mention may be made of the corresponding N-oxides.

The compounds of the formula (I) are capable of forming salts. Salts can be formed by the action of a base on those compounds of the formula (I) which bear an acidic hydrogen atom, for example in the case that $R^1$ contains a COOH group or a sulfonamide group —$NHSO_2$—. Examples of suitable bases are organic amines such as trialkylamines, morpholine, piperidine, or pyridine, and the hydroxides, carbonates and hydrogencarbonates of ammonium, alkali metals or alkaline earth metals, in particular sodium hydroxide, potassium hydroxide, sodium carbonate, potassium carbonate, sodium hydrogencarbonate and potassium hydrogencarbonate. These salts are compounds in which the acidic hydrogen is replaced by an agriculturally suitable cation, for example metal salts, especially alkali metal salts or alkaline earth metal salts, in particular sodium and potassium salts, or else ammonium salts, salts with organic amines or quaternary ammonium salts, for example with cations of the formula $[NRR'R''R''']^+$ in which R to R''' are each independently of one another an organic radical, especially alkyl, aryl, aralkyl or alkylaryl. Also useful are alkylsulfonium and alkylsulfoxonium salts, such as $(C_1-C_4)$-trialkylsulfonium and $(C_1-C_4)$-trialkylsulfoxonium salts.

The compounds of the formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid, or sulfonic acids, for example p-toluenesulfonic acid, onto a basic group, for example amino, alkylamino, dialkylamino, piperidino, morpholino or pyridino. In such a case, the salts will comprise the conjugated base of the acid as the anion.

Suitable substituents present in deprotonated form, such as, for example, sulfonic acids or carboxylic acids, may form inner salts with groups which for their part can be protonated, such as amino groups.

The compounds of the formula (I) and their salts are also referred to hereinafter as "compounds (I)" according to the invention or used in accordance with the invention.

In the general formula (I) and in all the other formulae of the present invention, the radicals alkyl, alkoxy, haloalkyl, haloalkoxy, alkylamino, alkylthio, haloalkylthio and the corresponding unsaturated and/or substituted radicals can in each case be straight-chain or branched in the carbon skeleton. Unless indicated specifically, preference is given for these radicals to the lower carbon skeletons, for example those having 1 to 6 carbon atoms, in particular 1 to 4 carbon atoms, or in the case of unsaturated groups having 2 to 6 carbon atoms, in particular 2 to 4 carbon atoms. Alkyl radicals, both alone and in composite definitions such as alkoxy, haloalkyl, etc., are, for example, methyl, ethyl, n-propyl or isopropyl, n-butyl, isobutyl, tert-butyl or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the definition of the possible unsaturated radicals corresponding to the alkyl radicals; where at least one double bond or triple bond is present, preferably one double bond or triple bond, respectively. Alkenyl is, for example, vinyl, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, ethynyl, propargyl, but-2-yn-1-yl, but-3-yn-1-yl and 1-methylbut-3-yn-1-yl.

Cycloalkyl groups are, for example, cyclopropyl, cyclobutyl, cyclopentyl, cyclohexyl, cycloheptyl and cyclooctyl. The cycloalkyl groups can be present in bi- or tricyclic form.

If haloalkyl groups and haloalkyl radicals of haloalkoxy, haloalkylthio, haloalkenyl, haloalkynyl etc. are stated, the lower carbon skeletons of these radicals having, for example, 1 to 6 carbon atoms or 2 to 6 carbon atoms, in particular 1 to 4 carbon atoms or preferably 2 to 4 carbon atoms, and the corresponding unsaturated and/or substituted radicals are in each case straight-chain or branched in the carbon skeleton. Examples are difluoromethyl, 2,2,2-trifluoroethyl, trifluoroallyl, 1-chloroprop-1-yl-3-yl.

Alkylene groups in these radicals are the lower carbon skeletons, for example those having 1 to 10 carbon atoms, in particular 1 to 6 carbon atoms, or preferably 2 to 4 carbon atoms, and also the corresponding unsaturated and/or substituted radicals in the carbon skeleton which may in each case be straight-chain or branched. Examples are methylene, ethylene, n- and isopropylene and n-, s-, iso-, t-butylene.

Hydroxyalkyl groups in these radicals are the lower carbon skeletons, for example those having 1 to 6 carbon atoms, in particular 1 to 4 carbon atoms, and also the corresponding unsaturated and/or substituted radicals in the carbon skeleton which may in each case be straight-chain or branched. Examples of these are 1,2-dihydroxyethyl and 3-hydroxypropyl.

Halogen is fluorine, chlorine, bromine or iodine. Haloalkyl, -alkenyl and -alkynyl are alkyl, alkenyl and alkynyl partly or fully substituted by halogen, preferably by fluorine, chlorine or bromine, especially by fluorine and/or chlorine, for example monohaloalkyl, perhaloalkyl, $CF_3$, $CF_2Cl$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same correspondingly applies to haloalkenyl and other halogen-substituted radicals.

Aryl is a monocyclic, bicyclic or polycyclic aromatic system, for example phenyl or naphthyl, preferably phenyl.

Primarily for reasons of higher herbicidal activity, better selectivity and/or better producibility, compounds of the general formula (I) according to the invention or their agrochemical salts or quaternary N derivatives are of particular interest in which individual radicals have one of the preferred meanings already specified or specified below, or in particular those in which one or more of the preferred meanings already specified or specified below occur in combination.

The abovementioned general or preferred radical definitions apply both to the end products of the general formula (I) and, correspondingly, to the starting materials and intermediates required in each case for the preparation. These radical definitions can be exchanged for one another as desired, i.e. including combinations between the given preferred ranges.

If tautomers are possible, the form described embraces all possible tautomeric structures. As shown below, the possible keto tautomers are also included, for example in the case $R^{2a}$=hydroxy.

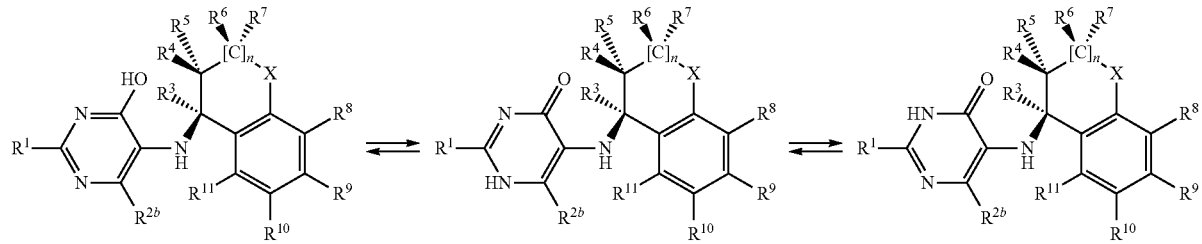

(I)

The present compounds of the general formula (I) have a chiral carbon atom which, in the structure shown below, is denoted by the marker (*).

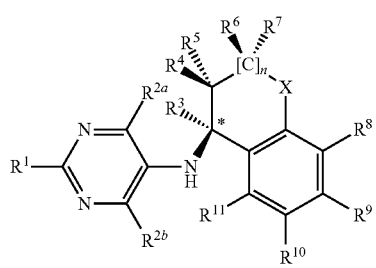

(I)

According to the rules of Cahn, Ingold and Prelog (CIP rules), this carbon atom can have either an (R) configuration or an (S) configuration.

The present invention encompasses compounds of the general formula (I) both with (S) and with (R) configuration, i.e. the present invention encompasses the compounds of the general formula (I) in which the carbon atom in question has
  (1) an (R) configuration; or
  (2) an (S) configuration.
In addition, the scope of the present invention also encompasses
  (3) any mixtures of compounds of the general formula (I) having an (R) configuration (compounds of the general formula (I-(R)) with compounds of the general formula (I) having an (S) configuration (compounds of the general formula (I-(S)),
where a racemic mixture of the compounds of the general formula (I) having (R) and (S) configuration is also embraced by the present invention.

However, within the context of the present invention, preference is given to using in particular compounds of the general formula (I) having (R) configuration with a selectivity of 60 to 100%, preferably 80 to 100%, in particular 90 to 100%, very particularly preferably 95 to 100%, where the particular (R) compound is present with an enantioselectivity of in each case more than 50% ee, preferably 60 to 100% ee, in particular 80 to 100% ee, very particularly 90 to 100% ee, most preferably 95 to 100% ee, based on the total content of (R) compound in question.

Accordingly, the present invention relates in particular to compounds of the general formula (I*) in which the stereochemical configuration on the carbon atom marked by (*) is present with a stereochemical purity of 60 to 100% (R), preferably 80 to 100% (R), in particular 90 to 100% (R), very particularly 95 to 100% (R).

Taking into account the Cahn, Ingold and Prelog rules, at the carbon atom marked (*) there may also be a situation in which, owing to the priority of the substituent in question, the (S) configuration is preferred at the carbon atom marked (*). This is the case, for example, when the radicals $R^4$ and/or $R^5$ correspond to a $C_1$-$C_6$-alkoxy radical.

Accordingly, within the context of the present invention, preference is given in particular to compounds of the general formula (I) whose spatial arrangement corresponds to that of the compounds of the general formula (I) where $R^4$ and $R^5$=hydrogen having the (R) configuration, with a selectivity of 60 to 100%, preferably 80 to 100%, in particular 90 to 100%, very particularly preferably 95 to 100%, where the respective (R)-analogous compound is present with an enantioselectivity of in each case more than 50% ee, preferably 60 to 100% ee, in particular 80 to 100% ee, very particularly preferably 90 to 100% ee, most preferably 95 to 100% ee, based on the total content of (R)-analogous compound in question. Accordingly, the present invention relates in particular to compounds of the general formula (I) in which the stereochemical configuration on the carbon atom marked by (*) is present with a stereochemical purity of 60 to 100% (R or R-analogous), preferably 80 to 100% (R or R-analogous), in particular 90 to 100% (R or R-analogous), very particularly 95 to 100% (R or R-analogous).

In particular, the compounds according to the invention of the general formula (I) may have further centers of chirality at the carbon atoms marked () and (*):

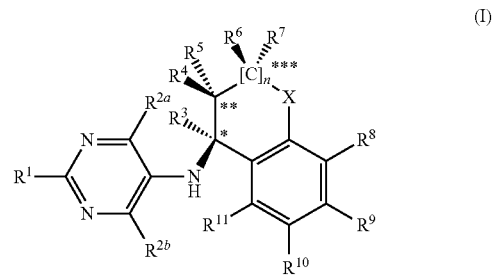

(I)

In the context of the present invention, any stereochemical configurations are possible at the carbon atoms marked (*), () and (*):

| Configuration carbon atom (*) | Configuration carbon atom () | Configuration carbon atom (*) |
|---|---|---|
| R | R | R |
| R | R | S |
| R | S | R |
| S | R | R |
| R | S | S |
| S | R | S |
| S | S | R |
| S | S | S |

In addition, depending on the respective radicals chosen, further stereoelements may be present in the compounds of the general formula (I) according to the invention.

When, for example, one or more alkenyl groups are present, diastereomers (Z and E isomers) may occur.

When, for example, one or more asymmetric carbon atoms are present, enantiomers and diastereomers may occur.

Corresponding stereoisomers can be obtained from the mixtures obtained in the preparation by customary separation methods, for example by chromatographic separation processes. It is equally possible to selectively prepare stereoisomers by using stereoselective reactions using optically active starting materials and/or auxiliaries. Accordingly, the invention also relates to all stereoisomers embraced by the general formula (I) but not shown in their specific stereoform, and to their mixtures.

For the possible combinations of the various substituents of the general formula (I) the general principles of the construction of chemical compounds have to be observed, i.e. the formula (I) does not comprise any compounds known to the person skilled in the art as being chemically impossible.

Examples of the compounds of the general formula (I) are shown below in tabular form.

In the table below:
"$StNR^3$" is the stereochemical arrangement at the carbon atom to which NH and $R^3$ are attached, "$StR^4R^5$" and "$StR^6R^7$" are analogously the carbon atoms to which the respective substituents are attached, the bond of the substituents is in each case on the left, if two binding sites are given for X, the left bond attaches to the aromatic ring and the right bond to the hydrogenated part of the bicyclic amine, cyprop denotes cyclopropyl, a hyphen "-" denotes a direct bond, and if n=0, the table has no entry in the corresponding field for $R^6$ and $R^7$.

| No. | $R^1$ | $R^{2a}$ | $R^{2b}$ | $R^3$ | St N $R^3$ | $R^4$ | $R^5$ | St $R^4$ $R^5$ | $R^6$ |
|---|---|---|---|---|---|---|---|---|---|
| 1. | $CF_3$ | H | H | H | rac | H | H | | H |
| 2. | $SOCH_3$ | H | H | H | rac | H | H | | H |
| 3. | $SO_2CH_3$ | H | H | H | rac | H | H | | H |
| 4. | $NO_2$ | H | H | H | rac | H | H | | H |
| 5. | CN | H | H | H | rac | H | H | | H |
| 6. | $CONH_2$ | H | H | H | rac | H | H | | H |
| 7. | $COOCH_3$ | H | H | H | rac | H | H | | H |
| 8. | $CONH\,CH_3$ | H | H | H | rac | H | H | | H |
| 9. | CONHcyprop | H | H | H | rac | H | H | | H |
| 10. | $CF_2CF_3$ | H | H | H | rac | H | H | | H |
| 11. | $CF_2CF_3$ | H | H | H | rac | H | H | | H |
| 12. | $CF_2CF_3$ | H | H | H | rac | H | H | | H |
| 13. | $CF_2CF_3$ | H | H | H | rac | H | H | | H |
| 14. | $CF_2CF_3$ | H | H | H | rac | H | H | | H |
| 15. | $CF_2CF_3$ | H | H | H | R | $CH_3$ | H | S | H |
| 16. | $CF_2CF_3$ | H | H | H | R | $CH_3$ | H | S | H |
| 17. | $CF_2CF_3$ | H | H | H | rac | H | H | | H |
| 18. | $CF_2CF_3$ | $OCH_3$ | H | H | R | H | H | | H |
| 19. | $CF_2CF_3$ | $OCH_3$ | H | H | rac | H | H | | H |
| 20. | $CF_2CF_3$ | $OCH_3$ | H | H | rac | H | H | | H |
| 21. | $CF_2CF_3$ | H | H | H | rac | H | H | | H |
| 22. | $CF_2CF_3$ | $OCH_3$ | H | H | R | H | H | | H |
| 23. | $CF_2CF_3$ | $OCH_3$ | H | H | R | $CH_3$ | H | S | H |
| 24. | $CF_2CF_3$ | $OCH_3$ | H | H | rac | H | H | | H |
| 25. | $CF_3$ | $OCH_3$ | H | H | R | $CH_3$ | H | S | H |
| 26. | $SOCH_3$ | H | H | $CH_3$ | rac | H | H | | H |
| 27. | $SO_2CH_3$ | H | H | $CH_3$ | rac | H | H | | H |
| 28. | $SO_2CH_3$ | H | H | $CH_3$ | rac | H | H | | H |
| 29. | $SO_2CH_3$ | H | H | $CH_3$ | rac | H | H | | H |
| 30. | $SO_2CH_3$ | H | H | $CH_2CH_2\,OCH_3$ | rac | H | H | | H |
| 31. | $SO_2CH_3$ | H | H | Ph | rac | H | H | | H |
| 32. | $SO_2CH_3$ | H | H | $COOCH_3$ | rac | H | H | | H |
| 33. | $SO_2CH_3$ | H | H | $CONH_2$ | rac | H | H | | H |
| 34. | $SO_2CH_3$ | H | H | $CONH_2$ | rac | H | H | | H |
| 35. | $CF_3$ | H | H | $CONH_2$ | rac | H | H | | H |
| 36. | CN | H | H | $CONH_2$ | rac | H | H | | H |
| 37. | $SO_2CH_3$ | H | H | H | rac | H | H | | |
| 38. | CN | H | H | H | rac | H | H | | |
| 39. | CF3 | H | H | H | rac | H | H | | |
| 40. | $SO_2CH_3$ | H | H | H | rac | H | H | | H |
| 41. | $SO_2CH_3$ | H | H | H | rac | H | H | | H |
| 42. | $SO_2CH_3$ | H | H | H | rac | H | H | | H |
| 43. | $SO_2CH_3$ | H | H | H | rac | H | H | | H |
| 44. | $SO_2CH_3$ | H | H | H | rac | H | H | | H |
| 45. | CN | H | H | H | rac | H | H | | H |
| 46. | $CF_3$ | H | H | H | rac | H | H | | H |
| 47. | $SO_2CH_3$ | H | H | H | rac | H | H | | H |

-continued

| | | | | | | | |
|---|---|---|---|---|---|---|---|
| 48. SO$_2$CH$_3$ | H | H | H | rac | H | H | H |
| 49. SO$_2$CH$_3$ | H | H | H | rac | H | H | H |
| 50. SO$_2$CH$_3$ | H | H | H | rac | H | H | H |
| 51. SO$_2$CH$_3$ | H | H | H | rac | H | H | H |
| 52. SO$_2$CH$_3$ | H | H | H | rac | H | H | H |
| 53. SO$_2$CH$_3$ | H | H | H | rac | H | H | H |
| 54. SO$_2$CH$_3$ | H | H | H | rac | H | H | H |
| 55. SO$_2$CH$_3$ | H | H | H | rac | H | H | H |
| 56. SO$_2$CH$_3$ | H | H | H | rac | H | H | H |
| 57. SO$_2$CH$_3$ | H | H | H | rac | H | H | H |
| 58. SO$_2$CH$_3$ | H | H | H | rac | H | H | H |
| 59. CF$_3$ | H | H | H | rac | H | H | H |
| 60. CN | H | H | H | rac | H | H | H |
| 61. SO$_2$CH$_3$ | H | H | H | rac | H | H | H |
| 62. SO$_2$CH$_3$ | H | H | H | rac | H | H | H |
| 63. CF$_2$CF$_3$ | H | H | H | R | H | H | H |
| 64. CN | H | H | H | rac | H | H | H |
| 65. SO$_2$CH$_3$ | H | H | H | rac | H | H | H |
| 66. SO$_2$CH$_3$ | CN | H | H | rac | H | H | H |
| 67. SO$_2$CH$_3$ | CONH$_2$ | H | H | rac | H | H | H |
| 68. SO$_2$CH$_3$ | COOH | H | H | rac | H | H | H |
| 69. SO$_2$CH$_3$ | COOCH$_3$ | H | H | rac | H | H | H |
| 70. CF$_3$ | H | H | H | rac | H | H | H |
| 71. SOCH$_3$ | OCH$_3$ | H | H | R | H | H | H |
| 72. SO$_2$CH$_3$ | OCH$_2$CH$_3$ | H | H | R | H | H | H |
| 73. SOCH$_3$ | OCH$_3$ | OCH$_3$ | H | R | H | H | H |
| 74. SOCH$_3$ | OCH$_3$ | OCH$_3$ | H | R | CH$_3$ | H | S H |
| 75. SO$_2$CH$_3$ | OCH$_3$ | OCH$_3$ | H | R | CH$_3$ | H | S H |
| 76. CN | H | H | H | R | CH$_3$ | H | S H |
| 77. COOCH$_2$CH$_3$ | H | H | H | R | CH$_3$ | H | S H |
| 78. COOCH$_3$ | H | H | H | R | CH$_3$ | H | S H |
| 79. CONH$_2$ | H | H | H | R | CH$_3$ | H | S H |
| 80. CON(CH$_3$)$_2$ | H | H | H | R | CH$_3$ | H | S H |
| 81. SO$_2$CH$_3$ | SO$_2$CH$_3$ | H | H | R | H | H | H |
| 82. COOCH$_2$CH$_3$ | H | H | H | R | H | H | H |
| 83. CN | H | H | H | R | H | H | H |
| 84. SO$_2$CH$_3$ | H | H | H | rac | H | H | H |
| 85. SO$_2$CH$_3$ | H | H | H | rac | H | H | H |
| 86. SO$_2$CH$_3$ | H | H | H | rac | H | H | H |
| 87. SO$_2$CH$_3$ | CONH$_2$ | H | H | R | H | H | H |
| 88. SO$_2$CH$_3$ | H | H | H | rac | CN | H | rac H |
| 89. SO$_2$CH$_3$ | CN | H | H | rac | H | H | |
| 90. SO$_2$CH$_3$ | CONH$_2$ | H | H | rac | H | H | H |
| 91. CF$_3$ | CONH$_2$ | H | H | rac | H | H | |
| 92. SO$_2$CH$_3$ | H | H | H | rac | H | H | H |
| 93. SO$_2$CH$_3$ | CONH$_2$ | H | H | R | CH$_3$ | H | S H |
| 94. SCH$_3$ | OH | CF$_3$ | H | R | CH$_3$ | H | S H |
| 95. SCH$_3$ | OH | CF$_2$H | H | R | CH$_3$ | H | S H |
| 96. SCH$_3$ | H | CF$_3$ | H | R | CH$_3$ | H | S H |
| 97. SO$_2$CH$_3$ | OH | CF$_3$ | H | R | CH$_3$ | H | S H |
| 98. SO$_2$CH$_3$ | OCH$_3$ | CF$_3$ | H | R | CH$_3$ | H | S H |
| 99. CN | CN | H | H | R | H | H | H |
| 100. CN | CN | CF$_3$ | H | R | H | H | H |
| 101. CN | CN | H | H | R | H | H | H |
| 102. CN | CN | CF$_3$ | H | R | H | H | H |
| 103. CN | CN | H | H | R | CH$_3$ | H | S H |
| 104. CN | CN | CF$_3$ | H | R | CH$_3$ | H | S H |
| 105. SO$_2$CH$_3$ | CONH$_2$ | H | H | R | H | H | H |
| 106. SO$_2$CH$_3$ | CN | H | H | R | H | H | H |
| 107. SO$_2$CH$_3$ | COOCH$_3$ | H | H | R | H | H | H |
| 108. SO$_2$CH$_3$ | CN | H | H | R | CH$_3$ | H | S H |
| 109. SO$_2$CH$_3$ | CN | H | H | R | H | H | H |
| 110. SO$_2$CH$_2$CH$_3$ | H | H | H | rac | H | H | H |
| 111. CF$_3$ | H | H | H | rac | H | H | H |
| 112. CF$_3$ | H | H | H | rac | H | H | H |
| 113. CF$_3$ | H | H | H | rac | H | H | H |
| 114. CF$_3$ | H | H | H | rac | H | H | H |
| 115. CF$_3$ | H | H | H | R | H | H | H |
| 116. CF$_3$ | H | H | H | R | CH$_3$ | H | S H |
| 117. CF$_3$ | H | H | H | R | H | H | H |
| 118. C$_6$H$_5$ | COOH | H | H | R | H | H | H |
| 119. C$_6$H$_5$ | CONH$_2$ | H | H | R | H | H | H |
| 120. C$_6$H$_5$ | H | H | H | R | H | H | H |
| 121. C$_6$H$_5$ | OH | CH$_3$ | H | R | H | H | H |
| 122. C$_6$H$_5$ | OH | cyprop | H | R | H | H | H |
| 123. C$_6$H$_5$ | OH | CH$_3$ | H | R | H | H | H |
| 124. C$_6$H$_5$ | OH | CH$_3$ | H | R | CH$_3$ | H | S H |
| 125. C$_6$H$_5$ | OH | cyprop | H | R | CH$_3$ | H | S H |
| 126. C$_6$H$_5$ | OH | cyprop | H | R | H | H | H |

| | | | | | | | | |
|---|---|---|---|---|---|---|---|---|
| 127. | CH₃ | COOH | H | H | R | H | H | | H |
| 128. | CH₃ | H | H | H | R | H | H | | H |
| 129. | SCH₃ | COOH | H | H | R | H | H | | H |
| 130. | SCH₃ | H | H | H | R | H | H | | H |
| 131. | SO₂CH₃ | H | H | H | R | H | H | | H |
| 132. | SO₂CH₃ | COOH | H | H | R | H | H | | H |
| 133. | SO₂CH₃ | COOCH₂CH₃ | H | H | R | H | H | | H |
| 134. | SO₂CH₃ | H | H | H | R | CH₃ | H | S | H |
| 135. | SO₂CH₃ | CONHCH₃ | H | H | R | CH₃ | H | S | H |
| 136. | SO₂CH₃ | CONHCH₃ | H | H | R | H | H | | H |
| 137. | SO₂CH₃ | CONHCH₂CH=CH₂ | H | H | R | H | H | | H |
| 138. | SO₂CH₃ | CONHcyprop | H | CH₃ | R | H | H | | H |
| 139. | SO₂CH₃ | CONHcyprop | H | H | R | CH₃ | H | S | H |
| 140. | SO₂CH₃ | CONHC₆H₅ | H | H | R | CH₃ | H | S | H |
| 141. | SO₂CH₃ | CONHC₆H₅ | H | H | R | H | H | | H |
| 142. | SO₂CH₃ | CONHCH₂C₆H₅ | H | H | R | H | H | | H |
| 143. | SO₂CH₃ | CF₃ | H | H | R | CH₃ | H | S | H |
| 144. | SO₂CH₃ | CH₃ | H | H | R | CH₃ | H | S | H |
| 145. | SO₂CH₃ | CH₃ | H | H | R | H | H | | H |
| 146. | SO₂CH₃ | CH₃ | H | H | R | CH₃ | H | S | H |
| 147. | SO₂CH₃ | OCH₃ | H | H | R | CH₃ | H | S | H |
| 148. | SO₂CH₃ | CH(CH₃)₂ | H | H | R | CH₃ | H | S | H |
| 149. | SO₂CH₃ | CH₃ | H | H | R | H | H | | H |
| 150. | SO₂CH₃ | CF₃ | H | H | R | H | H | | H |
| 151. | SO₂CH₃ | CF₂H | H | H | R | H | H | | H |
| 152. | SOCH₃ | CF₃ | H | H | R | H | H | | H |
| 153. | SOCH₃ | CN | H | H | R | H | H | | H |
| 154. | SO₂CH₃ | CF₃ | H | H | R | H | H | | H |
| 155. | SO₂CH₃ | CN | H | H | rac | H | H | | H |
| 156. | SO₂CH₃ | CF₃ | H | H | rac | H | H | | H |
| 157. | SO₂CH₃ | CH₃ | H | H | rac | H | H | | H |
| 158. | SO₂CH₃ | CN | H | H | rac | H | H | | H |
| 159. | SO₂CH₃ | H | H | H | rac | H | H | | H |
| 160. | SO₂CH₃ | H | H | H | rac | H | H | | H |
| 161. | SO₂CH₃ | H | H | H | rac | H | H | | H |
| 162. | SO₂CH₃ | H | H | H | rac | H | H | | H |
| 163. | SO₂CH₃ | H | H | H | rac | H | H | | H |
| 164. | SO₂CH₃ | CN | H | H | rac | H | H | | H |
| 165. | SO₂CH₃ | OCH₂C≡CH | H | H | rac | H | H | | H |
| 166. | SO₂CH₃ | C(CH₃)₃ | H | H | rac | H | H | | H |
| 167. | CN | CF₃ | H | H | rac | H | H | | H |
| 168. | SO₂CH₃ | H | H | H | rac | H | H | | H |
| 169. | SO₂CH₃ | H | H | H | rac | H | H | | CH₃ |
| 170. | SO₂CH₃ | H | H | H | rac | H | H | | C₆H₅ |
| 171. | SO₂CH₃ | H | H | H | rac | OH | H | rac | H |
| 172. | SO₂CH₃ | H | H | H | rac | OCH₃ | H | rac | H |
| 173. | SO₂CH₃ | H | H | H | rac | H | H | | H |
| 174. | SO₂CH₃ | H | H | H | rac | H | H | | H |
| 175. | SO₂CH₃ | COOH | H | H | rac | H | H | | H |
| 176. | SO₂CH₃ | CONH₂ | H | H | rac | H | H | | H |
| 177. | SO₂CH₃ | COOCH₃ | H | H | rac | H | H | | H |
| 178. | SO₂CH₃ | COOH | H | H | rac | H | H | | H |
| 179. | SO₂CH₃ | COOCH₃ | H | H | rac | H | H | | H |
| 180. | SO₂CH₃ | CONH₂ | H | H | rac | H | H | | H |
| 181. | SO₂CH₃ | CONH₂ | H | H | rac | H | H | | H |
| 182. | CN | COOH | H | H | rac | H | H | | H |
| 183. | CN | CONH₂ | H | H | rac | H | H | | H |
| 184. | CN | COOCH₃ | H | H | rac | H | H | | H |
| 185. | SO₂CH₃ | COOH | H | H | rac | H | H | | H |
| 186. | SO₂CH₃ | CONH₂ | H | H | rac | H | H | | H |
| 187. | SO₂CH₃ | COOCH₃ | H | H | rac | H | H | | H |
| 188. | SO₂CH₃ | COOCH₃ | H | H | rac | H | H | | H |
| 189. | SO₂CH₃ | CONHCH₃ | H | H | rac | H | H | | H |
| 190. | SO₂CH₃ | CONH₂ | H | H | rac | H | H | | H |
| 191. | SO₂CH₃ | COOH | H | H | rac | H | H | | H |
| 192. | SO₂CH₃ | COOCH₃ | H | H | rac | H | H | | H |
| 193. | SO₂CH₃ | COOCH₂CH₃ | H | H | rac | H | H | | H |
| 194. | SO₂CH₃ | COOCH₂CH₂OCH₃ | H | H | rac | H | H | | H |
| 195. | SO₂CH₃ | COOCH₂CH₂N(CH₃)₂ | H | H | rac | H | H | | H |
| 196. | SO₂CH₃ | CON(CH₂CH₃)₂ | H | H | rac | H | H | | H |
| 197. | SO₂CH₃ | CONH₂ | H | H | rac | H | H | | H |
| 198. | SO₂CH₃ | CON(CH₃)₂ | H | H | rac | H | H | | H |
| 199. | SO₂CH₃ | CONHcyprop | H | H | rac | H | H | | H |
| 200. | SO₂CH₃ | H | H | H | rac | CH₃ | H | rac | H |
| 201. | SO₂CH₃ | H | H | H | rac | CH₃ | H | rac | H |
| 202. | SO₂CH₃ | H | H | H | rac | CH₃ | H | rac | H |

-continued

| No. | R⁷ | | | | St | R⁶ | | | |
|---|---|---|---|---|---|---|---|---|---|
| 203. | SO₂CH₃ | H | H | H | rac | H | H | | |
| 204. | SO₂CH₃ | H | H | H | rac | H | H | | |
| 205. | SO₂CH₃ | H | H | H | rac | H | H | | |
| 206. | SO₂CH₃ | H | H | H | rac | H | H | | |
| 207. | SO₂CH₃ | COOH | H | H | rac | H | H | | |
| 208. | SO₂CH₃ | CONH₂ | H | H | rac | H | H | | |
| 209. | CN | H | H | H | rac | H | H | | |
| 210. | CF₃ | H | H | H | rac | H | H | | |
| 211. | CF₃ | CN | H | H | rac | H | H | | |
| 212. | CN | CN | H | H | rac | H | H | | |
| 213. | CN | CF₃ | H | H | rac | H | H | | |
| 214. | CH₃ | CH₃ | H | H | R | H | H | | H |
| 215. | CF₂H | H | H | H | R | H | H | | H |
| 216. | CHF—C₆H₅ | H | H | H | R | H | H | | H |
| 217. | OC₆H₅ | H | H | H | R | H | H | | H |
| 218. | OCH₂C≡CCH₃ | H | H | H | R | H | H | | H |
| 219. | OCH₂C≡CH | H | H | H | R | H | H | | H |
| 220. | OCH₂CH₃ | H | H | H | R | H | H | | H |
| 221. | OCH₃ | H | H | H | R | H | H | | H |
| 222. | OCH₂CF₃ | H | H | H | R | H | H | | H |
| 223. | CH₃ | CH₃ | H | H | R | CH₃ | H | S | H |
| 224. | CH(CH₃)₂ | CH₃ | H | H | R | CH₃ | H | S | H |
| 225. | SOCH₃ | H | H | H | R | CH₃ | H | S | H |
| 226. | CH(CH₃)₂ | H | H | H | R | CH₃ | H | S | H |
| 227. | OCH(CH₃)C≡CH | H | H | H | R | CH₃ | H | S | H |
| 228. | CH₂C₆H₄-4-Cl | H | H | H | R | CH₃ | H | S | H |
| 229. | OC₆H₅ | H | H | H | R | CH₃ | H | S | H |
| 230. | OCH₂C≡CH | H | H | H | R | CH₃ | H | S | H |
| 231. | OCH₂CH₃ | H | H | H | R | CH₃ | H | S | H |
| 232. | OCH₂C₆H₅ | H | H | H | R | CH₃ | H | S | H |
| 233. | OCH₃ | H | H | H | R | CH₃ | H | S | H |
| 234. | OCH₃ | H | H | H | R | H | H | | H |
| 235. | OCH₃ | CONH₂ | H | H | R | CH₃ | H | S | H |
| 236. | CONH₂ | CONH₂ | H | H | R | CH₃ | H | S | H |
| 237. | SCF₃ | CONH₂ | H | H | R | CH₃ | H | S | H |
| 238. | S(O)₂CF₃ | CONH₂ | H | H | R | CH₃ | H | S | H |
| 239. | OC₆H₅ | CONH₂ | H | H | R | CH₃ | H | S | H |
| 240. | OCH₃ | COOCH₃ | H | H | R | CH₃ | H | S | H |
| 241. | OCH₃ | COOH | H | H | R | CH₃ | H | S | H |
| 242. | OCH₂CH₃ | CN | H | H | R | CH₃ | H | S | H |
| 243. | OCH₃ | CN | H | H | R | CH₃ | H | S | H |
| 244. | OCH₂C≡CH | CN | H | H | R | CH₃ | H | S | H |
| 245. | NO₂ | CH₃ | H | H | R | H | H | | H |
| 246. | NO₂ | CH₃ | H | H | R | CH₃ | H | S | H |
| 247. | NO₂ | CH₃ | H | H | R | CH₃ | H | S | H |
| 248. | NO₂ | CH₃ | H | H | R | H | H | | H |
| 249. | NO₂ | CH₃ | H | H | R | H | H | | H |
| 250. | NO₂ | CH₃ | H | H | R | H | H | | H |
| 251. | NO₂ | CH₃ | H | H | rac | H | H | | H |
| 252. | NO₂ | CH₃ | H | H | rac | H | H | | H |
| 253. | NO₂ | CH₃ | H | H | rac | H | H | | H |
| 254. | NO₂ | CH₃ | H | H | rac | H | H | | H |
| 255. | SCH₃ | CH₃ | H | H | R | CH₃ | H | S | H |
| 256. | CF₃ | OH | CH₃ | H | R | CH₃ | H | S | H |
| 257. | CF₃ | CH₃ | CH₃ | H | R | CH₃ | H | S | H |
| 258. | SO₂CH₃ | CH₃ | CH₃ | H | R | CH₃ | H | S | H |
| 259. | SO₂CH₃ | OH | CH₃ | H | R | CH₃ | H | S | H |
| 260. | SO₂CH₃ | OH | CONH₂ | H | R | CH₃ | H | S | H |
| 261. | SO₂CH₃ | CH₃ | CONH₂ | H | R | CH₃ | H | S | H |
| 262. | SO₂CH₃ | CH₃ | CN | H | R | CH₃ | H | S | H |
| 263. | SO₂CH₃ | OH | CN | H | R | CH₃ | H | S | H |
| 264. | SO₂CH₃ | H | H | H | rac | CH₃ | CH₃ | | H |
| 265. | SO₂CH₃ | H | H | H | rac | —CH₂—CH₂— | | H | H |
| 266. | SO₂CH₃ | H | H | H | rac | CH₂CH₃ | CH₂CH₃ | | H |
| 267. | SO₂CH₃ | H | H | H | rac | H | H | | H |
| 268. | SO₂CH₃ | H | H | H | rac | H | H | | H |
| 269. | SO₂CH₃ | H | H | H | rac | H | H | | H |
| 270. | SO₂CH₃ | H | H | H | rac | H | H | | H |
| 271. | SO₂CH₃ | H | H | H | rac | H | H | | H |
| 272. | SO₂CH₃ | H | H | H | rac | H | H | | H |
| 273. | SO₂CH₃ | H | H | H | R | H | H | | H |
| 274. | SO₂CH₃ | H | H | H | rac | H | H | | H |

| No. | R⁷ | n | St R⁶ R⁷ | R⁸ | R⁹ | R¹⁰ | R¹¹ | X |
|---|---|---|---|---|---|---|---|---|
| 1. | H | 2 | | CH₃ | H | CH₃ | H | — |
| 2. | H | 2 | | CH₃ | H | CH₃ | H | — |

-continued

| | | | | | | | |
|---|---|---|---|---|---|---|---|
| 3. | H | 2 | CH₃ | H | CH₃ | H | — |
| 4. | H | 2 | CH₃ | H | CH₃ | H | — |
| 5. | H | 2 | CH₃ | H | CH₃ | H | — |
| 6. | H | 2 | CH₃ | H | CH₃ | H | — |
| 7. | H | 2 | CH₃ | H | CH₃ | H | — |
| 8. | H | 2 | CH₃ | H | CH₃ | H | — |
| 9. | H | 2 | CH₃ | H | CH₃ | H | — |
| 10. | H | 2 | CH₃ | H | CH₃ | H | — |
| 11. | H | 2 | H | H | H | H | — |
| 12. | H | 1 | H | H | H | H | O |
| 13. | H | 1 | H | H | H | H | S |
| 14. | H | 1 | H | H | H | H | — |
| 15. | H | 1 | H | H | H | H | — |
| 16. | H | 1 | H | H | CH₃ | H | — |
| 17. | H | 2 | F | H | H | H | — |
| 18. | H | 2 | H | H | H | H | — |
| 19. | H | 2 | CH₃ | H | CH₃ | H | — |
| 20. | H | 2 | H | H | CH₃ | H | — |
| 21. | H | 1 | H | H | CH₃ | H | — |
| 22. | H | 1 | H | H | CH₃ | H | — |
| 23. | H | 1 | H | H | CH₃ | H | — |
| 24. | H | 2 | H | H | F | H | — |
| 25. | H | 1 | H | H | CH₃ | H | — |
| 26. | H | 1 | H | H | CH₃ | H | — |
| 27. | H | 1 | H | H | CH₃ | H | — |
| 28. | H | 1 | H | H | H | H | — |
| 29. | H | 2 | H | H | H | H | — |
| 30. | H | 2 | H | H | H | H | — |
| 31. | H | 2 | H | H | H | H | — |
| 32. | H | 2 | H | H | H | H | — |
| 33. | H | 2 | H | H | H | H | — |
| 34. | H | 1 | H | H | H | H | — |
| 35. | H | 1 | H | H | H | H | — |
| 36. | H | 1 | H | H | H | H | — |
| 37. | | 0 | CH₃ | CH₃ | H | H | O |
| 38. | | 0 | CH₃ | CH₃ | H | H | O |
| 39. | | 0 | CH₃ | CH₃ | H | H | O |
| 40. | H | 1 | H | Cl | H | H | — |
| 41. | H | 1 | H | F | H | H | — |
| 42. | H | 1 | H | H | F | H | — |
| 43. | H | 1 | H | H | Cl | H | — |
| 44. | H | 1 | H | OCH₃ | OCH₃ | H | — |
| 45. | H | 1 | H | Cl | H | H | — |
| 46. | H | 1 | H | Cl | H | H | — |
| 47. | H | 1 | H | H | CH₃ | H | S |
| 48. | H | 1 | H | H | F | H | S |
| 49. | H | 1 | CH₃ | H | CH₃ | H | S |
| 50. | H | 1 | Cl | H | Cl | H | S |
| 51. | H | 1 | CH₃ | H | OCH₃ | H | S |
| 52. | H | 1 | OCH₃ | H | H | H | S |
| 53. | H | 1 | OCH₂CH₃ | H | H | H | S |
| 54. | H | 1 | N(CH₃)₂ | H | H | H | S |
| 55. | H | 1 | H | H | Br | H | S |
| 56. | H | 1 | H | H | C≡CH | H | S |
| 57. | H | 1 | H | H | C≡CCH₃ | H | S |
| 58. | H | 1 | H | H | CN | H | S |
| 59. | H | 1 | H | H | CH₃ | H | S |
| 60. | H | 1 | H | H | CH₃ | H | S |
| 61. | H | 1 | H | H | H | H | S |
| 62. | H | 1 | CH₃ | H | CH₃ | H | O |
| 63. | H | 2 | H | H | H | H | — |
| 64. | H | 1 | H | H | CH₂CH₃ | H | O |
| 65. | H | 1 | H | H | CH₂CH₃ | H | O |
| 66. | H | 1 | H | H | CH₂CH₃ | H | O |
| 67. | H | 1 | H | H | CH₂CH₃ | H | O |
| 68. | H | 1 | H | H | CH₂CH₃ | H | O |
| 69. | H | 1 | H | H | CH₂CH₃ | H | O |
| 70. | H | 1 | H | H | CH₂CH₃ | H | O |
| 71. | H | 2 | H | H | H | H | — |
| 72. | H | 2 | H | H | H | H | — |
| 73. | H | 1 | H | H | CH₃ | H | — |
| 74. | H | 1 | H | H | CH₃ | H | — |
| 75. | H | 1 | H | H | CH₃ | H | — |
| 76. | H | 1 | H | H | CH₃ | H | — |
| 77. | H | 1 | H | H | CH₃ | H | — |
| 78. | H | 1 | H | H | CH₃ | H | — |
| 79. | H | 1 | H | H | CH₃ | H | — |
| 80. | H | 1 | H | H | CH₃ | H | — |
| 81. | H | 2 | H | H | H | H | — |

-continued

| | | | | | | | |
|---|---|---|---|---|---|---|---|
| 82. | H | 2 | H | H | H | H | — |
| 83. | H | 2 | H | H | H | H | — |
| 84. | H | 1 | H | OCH₃ | H | H | O |
| 85. | H | 1 | OCH₃ | OCH₃ | H | H | O |
| 86. | H | 1 | H | OCH₃ | OCH₃ | H | O |
| 87. | H | 2 | H | H | H | H | — |
| 88. | H | 1 | H | H | H | H | — |
| 89. | | 0 | H | H | H | H | O |
| 90. | H | 1 | F | H | H | H | — |
| 91. | | 0 | H | H | H | H | O |
| 92. | H | 1 | H | H | H | H | O |
| 93. | H | 1 | H | H | CH₃ | H | — |
| 94. | H | 1 | H | H | CH₃ | H | — |
| 95. | H | 1 | H | H | CH₃ | H | — |
| 96. | H | 1 | H | H | CH₃ | H | — |
| 97. | H | 1 | H | H | CH₃ | H | — |
| 98. | H | 1 | H | H | CH₃ | H | — |
| 99. | H | 1 | H | H | H | H | — |
| 100. | H | 1 | H | H | H | H | — |
| 101. | H | 2 | H | H | H | H | — |
| 102. | H | 2 | H | H | H | H | — |
| 103. | H | 1 | H | H | CH₃ | H | — |
| 104. | H | 1 | H | H | CH₃ | H | — |
| 105. | H | 1 | H | H | H | H | — |
| 106. | H | 1 | H | H | H | H | — |
| 107. | H | 1 | H | H | H | H | — |
| 108. | H | 1 | H | H | CH₃ | H | — |
| 109. | H | 2 | H | H | H | H | — |
| 110. | H | 1 | H | H | F | H | — |
| 111. | H | 1 | CH₃ | H | H | H | — |
| 112. | H | 1 | Cl | H | H | H | — |
| 113. | H | 1 | H | H | F | H | — |
| 114. | H | 1 | H | H | CH₂CH₃ | H | — |
| 115. | H | 1 | H | H | H | H | — |
| 116. | H | 1 | H | H | CH₃ | H | — |
| 117. | H | 2 | H | H | H | H | — |
| 118. | H | 2 | H | H | H | H | — |
| 119. | H | 2 | H | H | H | H | — |
| 120. | H | 2 | H | H | H | H | — |
| 121. | H | 2 | H | H | H | H | — |
| 122. | H | 2 | H | H | H | H | — |
| 123. | H | 1 | H | H | H | H | — |
| 124. | H | 1 | H | H | CH₃ | H | — |
| 125. | H | 1 | H | H | CH₃ | H | — |
| 126. | H | 1 | H | H | H | H | — |
| 127. | H | 2 | H | H | H | H | — |
| 128. | H | 2 | H | H | H | H | — |
| 129. | H | 2 | H | H | H | H | — |
| 130. | H | 2 | H | H | H | H | — |
| 131. | H | 1 | H | H | H | H | — |
| 132. | H | 1 | H | H | H | H | — |
| 133. | H | 1 | H | H | H | H | — |
| 134. | H | 1 | H | H | CH₃ | H | — |
| 135. | H | 1 | H | H | CH₃ | H | — |
| 136. | H | 2 | H | H | H | H | — |
| 137. | H | 2 | H | H | H | H | — |
| 138. | H | 2 | H | H | H | H | — |
| 139. | H | 1 | H | H | CH₃ | H | — |
| 140. | H | 1 | H | H | CH₃ | H | — |
| 141. | H | 2 | H | H | H | H | — |
| 142. | H | 2 | H | H | H | H | — |
| 143. | H | 1 | H | H | H | H | — |
| 144. | H | 1 | H | H | CH₃ | H | — |
| 145. | H | 1 | H | H | CH₃ | H | — |
| 146. | H | 1 | H | H | H | H | — |
| 147. | H | 1 | H | H | CH₃ | H | — |
| 148. | H | 1 | H | H | CH₃ | H | — |
| 149. | H | 2 | H | H | H | H | — |
| 150. | H | 2 | H | H | H | H | — |
| 151. | H | 2 | H | H | H | H | — |
| 152. | H | 2 | H | H | H | H | — |
| 153. | H | 2 | H | H | H | H | — |
| 154. | H | 1 | H | H | H | H | O |
| 155. | H | 1 | H | H | H | H | O |
| 156. | H | 1 | H | H | CH₃ | H | O |
| 157. | H | 1 | H | H | CH₃ | H | O |
| 158. | H | 1 | H | H | CH₃ | H | O |
| 159. | H | 2 | H | H | CH₃ | H | — |
| 160. | H | 2 | F | H | CH₃ | H | — |

-continued

| | | | | | | | |
|---|---|---|---|---|---|---|---|
| 161. | H | 1 | F | H | CH$_3$ | H | O |
| 162. | H | 1 | CH$_3$ | H | F | H | O |
| 163. | H | 1 | CH$_3$ | H | H | H | O |
| 164. | H | 1 | CH$_3$ | H | H | H | O |
| 165. | H | 1 | CH$_3$ | H | H | H | O |
| 166. | H | 1 | CH$_3$ | H | H | H | O |
| 167. | H | 1 | CH$_3$ | H | H | H | O |
| 168. | H | 2 | CH$_3$ | H | H | H | — |
| 169. | CH$_3$ | 1 | CH$_3$ | H | H | H | O |
| 170. | H | 1 rac | H | H | H | H | O |
| 171. | H | 1 | H | H | H | H | — |
| 172. | H | 1 | H | H | H | H | — |
| 173. | H | 1 | H | H | OCH$_3$ | H | — |
| 174. | H | 2 | H | OCH$_3$ | OCH$_3$ | H | — |
| 175. | H | 2 | H | OCH$_3$ | OCH$_3$ | H | — |
| 176. | H | 2 | H | OCH$_3$ | OCH$_3$ | H | — |
| 177. | H | 2 | H | OCH$_3$ | OCH$_3$ | H | — |
| 178. | H | 1 | H | H | OCH$_3$ | H | — |
| 179. | H | 1 | H | H | OCH$_3$ | H | — |
| 180. | H | 1 | H | H | OCH$_3$ | H | — |
| 181. | H | 1 | H | OCH$_3$ | OCH$_3$ | H | — |
| 182. | H | 1 | CH$_3$ | H | H | H | O |
| 183. | H | 1 | CH$_3$ | H | H | H | O |
| 184. | H | 1 | CH$_3$ | H | H | H | O |
| 185. | H | 1 | CH$_3$ | H | H | H | O |
| 186. | H | 1 | CH$_3$ | H | H | H | O |
| 187. | H | 1 | CH$_3$ | H | H | H | O |
| 188. | H | 1 | F | H | H | H | O |
| 189. | H | 1 | F | H | H | H | O |
| 190. | H | 1 | F | H | H | H | O |
| 191. | H | 2 | CH$_3$ | H | CH$_3$ | H | — |
| 192. | H | 2 | CH$_3$ | H | CH$_3$ | H | — |
| 193. | H | 2 | CH$_3$ | H | CH$_3$ | H | — |
| 194. | H | 2 | CH$_3$ | H | CH$_3$ | H | — |
| 195. | H | 2 | CH$_3$ | H | CH$_3$ | H | — |
| 196. | H | 2 | CH$_3$ | H | CH$_3$ | H | — |
| 197. | H | 2 | CH$_3$ | H | CH$_3$ | H | — |
| 198. | H | 2 | CH$_3$ | H | CH$_3$ | H | — |
| 199. | H | 2 | CH$_3$ | H | CH$_3$ | H | — |
| 200. | H | 2 | H | H | CH$_3$ | H | — |
| 201. | H | 1 | H | H | CH$_3$ | H | O |
| 202. | H | 1 | H | H | H | H | O |
| 203. | | 0 | H | H | H | H | —CH$_2$—O— |
| 204. | | 0 | H | H | Br | H | —CH$_2$—O— |
| 205. | | 0 | H | H | CH=CH$_2$ | H | —CH$_2$—O— |
| 206. | | 0 | H | H | C≡CH | H | —CH$_2$—O— |
| 207. | | 0 | H | H | H | H | —CH$_2$—O— |
| 208. | | 0 | H | H | H | H | —CH$_2$—O— |
| 209. | | 0 | H | H | H | H | —CH$_2$—O— |
| 210. | | 0 | H | H | H | H | —CH$_2$—O— |
| 211. | | 0 | H | H | H | H | —CH$_2$—O— |
| 212. | | 0 | H | H | H | H | —CH$_2$—O— |
| 213. | | 0 | H | H | H | H | —CH$_2$—O— |
| 214. | H | 2 | H | H | H | H | — |
| 215. | H | 2 | H | H | H | H | — |
| 216. | H | 2 | H | H | H | H | — |
| 217. | H | 2 | H | H | H | H | — |
| 218. | H | 2 | H | H | H | H | — |
| 219. | H | 2 | H | H | H | H | — |
| 220. | H | 2 | H | H | H | H | — |
| 221. | H | 2 | H | H | H | H | — |
| 222. | H | 2 | H | H | H | H | — |
| 223. | H | 1 | H | H | CH$_3$ | H | — |
| 224. | H | 1 | H | H | CH$_3$ | H | — |
| 225. | H | 1 | H | H | CH$_3$ | H | — |
| 226. | H | 1 | H | H | CH$_3$ | H | — |
| 227. | H | 1 | H | H | CH$_3$ | H | — |
| 228. | H | 1 | H | H | CH$_3$ | H | — |
| 229. | H | 1 | H | H | CH$_3$ | H | — |
| 230. | H | 1 | H | H | CH$_3$ | H | — |
| 231. | H | 1 | H | H | CH$_3$ | H | — |
| 232. | H | 1 | H | H | CH$_3$ | H | — |
| 233. | H | 1 | H | H | CH$_3$ | H | — |
| 234. | H | 1 | H | H | CH$_3$ | H | — |
| 235. | H | 1 | H | H | CH$_3$ | H | — |
| 236. | H | 1 | H | H | CH$_3$ | H | — |
| 237. | H | 1 | H | H | CH$_3$ | H | — |
| 238. | H | 1 | H | H | CH$_3$ | H | — |
| 239. | H | 1 | H | H | CH$_3$ | H | — |

-continued

| # | | | | | | | |
|---|---|---|---|---|---|---|---|
| 240. | H | 1 | H | H | CH₃ | H | — |
| 241. | H | 1 | H | H | CH₃ | H | — |
| 242. | H | 1 | H | H | CH₃ | H | — |
| 243. | H | 1 | H | H | CH₃ | H | — |
| 244. | H | 1 | H | H | CH₃ | H | — |
| 245. | H | 1 | H | H | CH₃ | H | — |
| 246. | H | 1 | H | H | CH₃ | H | — |
| 247. | H | 1 | H | H | H | H | — |
| 248. | H | 1 | H | H | H | H | — |
| 249. | H | 2 | H | H | H | H | — |
| 250. | H | 2 | H | H | CH₃ | H | — |
| 251. | H | 2 | CH₃ | H | CH₃ | H | — |
| 252. | H | 1 | CH₃ | H | H | H | O |
| 253. | H | 1 | F | H | H | H | O |
| 254. | H | 2 | F | H | H | H | — |
| 255. | H | 1 | H | H | CH₃ | H | — |
| 256. | H | 1 | H | H | CH₃ | H | — |
| 257. | H | 1 | H | H | CH₃ | H | — |
| 258. | H | 1 | H | H | CH₃ | H | — |
| 259. | H | 1 | H | H | CH₃ | H | — |
| 260. | H | 1 | H | H | CH₃ | H | — |
| 261. | H | 1 | H | H | CH₃ | H | — |
| 262. | H | 1 | H | H | CH₃ | H | — |
| 263. | H | 1 | H | H | CH₃ | H | — |
| 264. | H | 1 | H | H | H | H | — |
| 265. | H | 1 | H | H | H | H | — |
| 266. | H | 1 | H | H | H | H | — |
| 267. | H | 1 | H | H | H | H | C=O |
| 268. | H | 1 | H | H | H | H | CHCH₃ |
| 269. | H | 1 | H | H | H | H | NCH₃ |
| 270. | H | 1 | H | H | H | H | NH |
| 271. | H | 1 | H | H | H | H | C(CH₃)₂ |
| 272. | | 0 | H | H | H | H | —CH₂—S— |
| 273. | H | 2 | H | H | H | H | — |
| 274. | H | 2 | F | H | H | H | — |

The present invention furthermore provides processes for preparing corresponding compounds of the general formula (I) and/or salts thereof and/or agrochemically acceptable quaternized nitrogen derivatives thereof:

a.) To prepare compounds of the general formula (I)

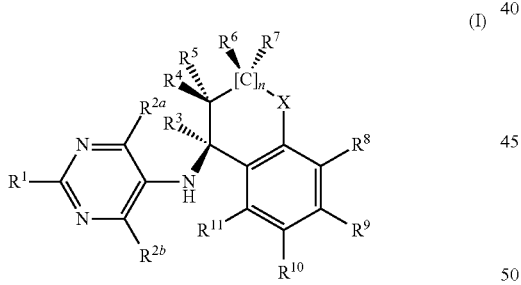

in which the radicals $R^1$ to $R^{11}$ and X and also n have the above meanings, a compound of the general formula (II)

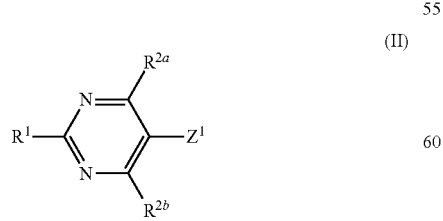

in which $R^1$ and $R^{2a}$ and also $R^{2b}$ have the above meaning and $Z^1$ is an exchangeable radical or a leaving group, is reacted with an amine of the general formula (III) or an acid addition salt of the amine of the general formula (III)

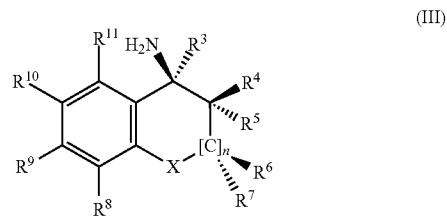

where the radicals $R^3$ to $R^{11}$ and X and also n have the above meaning.

The exchangeable radical $Z^1$ or the leaving group $Z^1$ is in particular fluorine, chlorine, bromine, iodine, a $(C_1\text{-}C_4)$-alkylsulfonyl, an unsubstituted or a substituted phenyl-$(C_1\text{-}C_4)$-alkylsulfonyl or a $(C_1\text{-}C_4)$-alkylphenyl-sulfonyl.

Particularly preferred as leaving groups for $Z^1$ are bromine, chlorine or fluorine (see A. Synthesis examples, in particular Ex. 64, Ex. 92, Ex. 115 and Ex. 273).

The compounds of the general formula (II) are commercially available or can be prepared by known methods. It is optionally also possible to use compounds of the formula (II) where $R^{2a}$ is COOH, where in this case the COOH is decarboxylated and converted into hydrogen under the chosen reaction conditions. It is optionally also possible to use compounds of the formula (II) where $R^{2a}$ is $COOR^{2aa}$, where $R^{2aa}$ is $(C_1\text{-}C_4)$-alkyl, $(C_1\text{-}C_4)$-alkylphenyl or another ester-forming group, and then to hydrolyze the $COOR^{2aa}$ in situ under the chosen reaction conditions or to hydrolyze subsequently, to convert into $R^{2a}$=COOH, then to decarboxylate the COOH group and to convert it into hydrogen.

The reaction may optionally also be catalyzed by various auxiliaries, for example by the reagents potassium phosphate, copper(I) iodide and N,N-diethyl-2-hydroxybenzamide, or in the sense of a Buchwald-Hartwig coupling by special transition metal catalyst systems.

For example, 2-methylthio-5-chloropyrimidine-4-carboxylic acids can be prepared from mucochloric acid and S-methylthiuronium sulfate (Liang, Yong-min, Luo, Sheng-jun, Zhang, Zhao-xin and Yong-xiang (2002) 'EFFICIENT SYNTHESIS OF A NEW PYRIMIDINE DERIVATIVE', Synthetic Communications, 32:1, 153-157, http://dx.doi.org/10.1081/SCC-120001523) and then be oxidized to the methanesulfonyl derivative. Analogously, it is also possible to employ mucobromic acid (Collect. Czech. Chem. Commun. 1949, 14, 223; Tetrahedron. Lett. 1976, 693).

The amines of the general formula (III) or the acid addition salts thereof are commercially available, or their synthesis is described in WO2004/069814 A1.

b.) Optionally, analogously to the process described in WO2004/92166 A2, page 68, 5-aminopyrimidines can be reacted with ketones that are commercially available or can be prepared by known methods and be hydrogenated, for example, with sodium triacetoxyborohydride to give compounds corresponding to formula (I).

Optionally, the reaction may also be carried out in two separate partial steps by initially reacting the amine with ketones that are commercially available or can be prepared by known methods to give an imine, and then hydrogenating the intermediate thus obtained.

c.) To prepare compounds of the general formula (I), it is possible to use compounds as precursors and to convert these into other compounds according to the invention.

(1) For example, derivatives of the formula (I) where $R^1$, $R^{2a}$, $R^{2b}$ or $R^{10}$=Hal, in particular iodine or bromine can be reacted with acetylenes or trimethylsilyl-protected acetylenes under transition metal catalysis, for example with bis(triphenylphosphine)palladium(II) chloride in protic or aprotic solvents and with added base at temperatures between 20 and 150° C. to give compounds of the formula (I) where $R^1$, $R^{2a}$, $R^{2b}$ or $R^{10}$=alkynyl.

(2) For example, derivatives of the formula (I) where $R^1$ or $R^{2a}$ or $R^{2b}$=CN can be hydrolyzed under acid or base catalysis, the carboxylic acids obtained in this manner can be converted by known processes into acid chlorides and these in turn can be converted into amides.

(3) For example, derivatives of the formula (I) where $R^1$ or $R^{2a}$ or $R^{2b}$=Hal, in particular chlorine or bromine, or $SO_2Me$ or $(C_1-C_6)$-alkylsulfonyl or phenyl $(C_1-C_6)$-alkylsulfonyl can be converted in protic or aprotic solvents and with added base at temperatures between 100 and 200° C. by reaction with alkoxides or amines into compounds of the formula (I) where $R^1$ or $R^{2a}$ or $R^{2b}$=alkoxyalkyl or aminoalkyl or diaminoalkyl.

(4) For example, derivatives of the formula (I) where $R^1$ or $R^{2a}$ or $R^{2b}$=COOH can be converted into acid chlorides or mixed anhydrides and then be reacted with alcohols or amines to give the corresponding carboxylic ester or amides.

(5) For example, derivatives of the formula (I) where $R^1$ or $R^{2a}$ or $R^{2b}$=$CONH_2$ can be converted by dehydration with phosphorus oxychloride into the corresponding nitriles.

(6) For example, derivatives of the formula (I) where $R^1$ or $R^{2a}$ or $R^{2b}$=$SO_2Me$ or $(C_1-C_6)$-alkylsulfonyl or phenyl $(C_1-C_6)$-alkylsulfonyl can be converted with formanilides (cf.: Ihare Chem Ind (TSUB) J6-2099305 and J6-2106084) into the corresponding anilides.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the work-up or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be purchased, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in Chem Files, Vol. 4, No. 1, Polymer-Supported Scavengers and Reagents for Solution-Phase Synthesis (Sigma-Aldrich).

Aside from the methods described here, the compounds of the general formula (I) and salts thereof can be prepared completely or partially by solid-phase supported methods. For this purpose, individual intermediates or all intermediates in the synthesis or a synthesis adapted for the corresponding procedure are bound to a synthesis resin. Solid phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid phase-supported synthesis methods permits a number of protocols known from the literature, and these may again be executed manually or in an automated manner. The reactions can be performed, for example, by means of IRORI technology in microreactors from Nexus Biosystems, 12140 Community Road, Poway, Calif. 92064, USA.

Both in the solid and in the liquid phase, individual or several synthesis steps may be supported by the use of microwave technology. The specialist literature describes a series of experimental protocols, for example in Microwaves in Organic and Medicinal Chemistry (editor C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

On account of the herbicidal property of the compounds of the general formula (I), the invention also further provides the use of the compounds of the general formula (I) according to the invention as herbicides for controlling harmful plants.

Herbicides are used in agriculturally utilized crops during various cultivation phases. Thus, the application of some products even takes place before or during sowing. Others are applied before the crop plant emerges, i.e. before the seedling breaks through the earth's surface (pre-emergence herbicides). Finally, post-emergence herbicides are used if either already the seed leaves or foliage leaves have been formed by the crop plant.

Here, the compounds according to the invention can be used either pre-emergence or post-emergence, with use of the compounds according to the invention pre-emergence being preferred.

The pre-emergence treatment includes both the treatment of the area under cultivation prior to sowing (ppi=pre plant incorporation) and the treatment of the sown areas of cultivation which do not yet sustain any growth.

The compounds of the formula (I) according to the invention and their salts, also referred to synonymously below together as compounds of the formula (I), have excellent herbicidal efficacy against a broad spectrum of economically important monocotyledonous and dicotyledonous harmful plants. Difficult-to-control perennial weeds which produce shoots from rhizomes, root stocks or other perennial organs are also well controlled by the active compounds. Here, it is immaterial whether the substances are applied by the presowing method, the pre-emergence method or the post-emergence method.

Specific examples may be mentioned of some representatives of the monocotyledonous and dicotyledonous weed flora which can be controlled by the compounds of the general formula (I) according to the invention, without the enumeration being restricted to certain species.

On the side of the monocotyledonous weed species, e.g. *Agrostis, Alopecurus, Apera, Avena, Brachicaria, Bromus, Dactyloctenium, Digitaria, Echinochloa, Eleocharis, Eleusine, Festuca, Fimbristylis, Ischaemum, Lolium, Monochoria, Panicum, Paspalum, Phalaris, Phleum, Poa, Sagittaria, Scirpus, Setaria, Sphenoclea,* and also *Cyperus* species predominantly from the annual group and on the sides of the perennial species *Agropyron, Cynodon, Imperata* and *Sorghum* and also perennial *Cyperus* species are well controlled.

In the case of dicotyledonous weed species, the spectrum of action extends to species such as, for example, *Galium, Viola, Veronica, Lamium, Stellaria, Amaranthus, Sinapis, Ipomoea, Matricaria, Abutilon* and *Sida* on the annual side, and *Convolvulus, Cirsium, Rumex* and *Artemisia* in the case of the perennial weeds. Moreover, herbicidal effect in the case of dicotyledonous weeds such as *Ambrosia, Anthemis, Carduus, Centaurea, Chenopodium, Cirsium, Convolvulus, Datura, Emex, Galeopsis, Galinsoga, Lepidium, Lindernia, Papaver, Portlaca, Polygonum, Ranunculus, Rorippa, Rotala, Seneceio, Sesbania, Solanum, Sonchus, Taraxacum, Trifolium, Urtica* and *Xanthium* is observed.

If the compounds of the general formula (I) according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the active compounds of the general formula (I) are applied post-emergence to the green parts of the plants, growth likewise stops drastically a very short time after the treatment, and the weed plants remain at the growth stage of the point of time of application, or they die completely after a certain time, so that in this manner competition by the weeds, which is harmful to the crop plants, is eliminated very early and in a sustained manner.

Although the compounds of the general formula (I) according to the invention have excellent herbicidal activity in respect of monocotyledonous and dicotyledonous weeds, crop plants of economically important crops, such as, for example, wheat, barley, rye, rice, corn, sugar beet, cotton, oilseed rape and soybean, are only damaged negligibly, if at all. This is why the present compounds are highly suitable for the selective control of unwanted plant growth in agriculturally useful plants.

In addition, the substances of the general formula (I) according to the invention have excellent growth regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since lodging can be reduced, or prevented completely, hereby.

By virtue of their herbicidal and plant-growth-regulatory properties, the active compounds can also be employed for controlling harmful plants in crops of known genetically modified plants or genetically modified plants still to be developed. In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material. Other particular properties may be tolerance or resistance to abiotic stressors, for example heat, low temperatures, drought, salinity and ultraviolet radiation.

It is preferred to use the compounds of the general formula (I) according to the invention or salts thereof in economically important transgenic crops of useful plants and ornamental plants, for example of cereals such as wheat, barley, rye, oats, sorghum and millet, rice, cassava and corn or else crops of sugar beet, cotton, soybean, oilseed rape, potato, tomato, peas and other vegetables.

It is preferred to be able to employ the compounds of the general formula (I) as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with altered properties can be generated with the aid of recombinant methods (see, for example, EP 0221044, EP 0131624). For example, the following have been described in several cases:

- genetic modifications of crop plants for the purpose of modifying the starch synthesized in the plants (for example WO 92/011376, WO 92/014827, WO 91/019806),
- transgenic crop plants which are resistant to certain herbicides of the glufosinate type (cf., for example, EP 0242236, EP 0242246) or the glyphosate type (WO 92/000377) or the sulfonylurea type (EP 0257993, U.S. Pat. No. 5,013,659),
- transgenic crop plants, for example cotton, which is capable of producing Bacillus thuringiensis toxins (Bt toxins), which make the plants resistant to certain pests (EP 0142924, EP 0193259),
- transgenic crop plants with a modified fatty acid composition (WO 91/013972),
- genetically modified crop plants with novel constituents or secondary metabolites, for example novel phytoalexins, which bring about an increased disease resistance (EP 0309862, EP 0464461),
- genetically modified plants with reduced photorespiration, which feature higher yields and higher stress tolerance (EP 0305398),
- transgenic crop plants which produce pharmaceutically or diagnostically important proteins ("molecular pharming"),
- transgenic crop plants which are distinguished by higher yields or better quality,
- transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

To carry out such recombinant manipulations, nucleic acid molecules which allow mutagenesis or a sequence change by recombination of DNA sequences can be introduced into plasmids. For example, base substitutions can be carried out, part-sequences can be removed, or natural or synthetic sequences may be added with the aid of standard methods. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized may be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

It is preferred to employ the compounds of the general formula (I) according to the invention in transgenic crops which are resistant to growth regulators such as, for example, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosate, glufosinate or benzoylisoxazoles and analogous active substances.

When the active compounds of the general formula (I) according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds of the general formula (I) according to the invention as herbicides for controlling harmful plants in transgenic crop plants.

The compounds of the general formula (I) can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], Volume 7, C. Hanser Verlag Munich, 4. ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J., H. v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie" [Chemical Technology], volume 7, C. Hanser Verlag Munich, 4th ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'dinaphthylmethane-6,6'-disulfonate, sodium dibutylnaphthalenesulfonate or else sodium oleylmethyltauride. To produce the wettable powders, the herbicidal active ingredients are ground finely, for example in customary apparatus such as hammer mills, blower mills and air-jet mills, and simultaneously or subsequently mixed with the formulation auxiliaries.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may be, for example: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophillite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, e.g. oil-in-water emulsions (EW), can be prepared, for example, by means of stirrers, colloid mills and/or static mixers using aqueous organic solvents and if appropriate surfactants, as have for example already been listed above in connection with the other types of formulation.

Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations comprise generally from 0.1 to 99% by weight, in particular from 0.1 to 95% by weight, of active compound of the formula (I).

In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

The compounds of the general formula (I) or salts thereof can be employed as such or in the form of their preparations (formulations) combined with other pesticidally active compounds, such as, for example, insecticides, acaricides, nematicides, herbicides, fungicides, safeners, fertilizers and/or growth regulators, for example as finished formulation or as tank mix.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as are described in, for example, Weed Research 26 (1986) 441-445 or "The Pesticide Manual", 15th edition, The British Crop Protection Council and the Royal Soc. of Chemistry, 2006 and the literature cited therein. Known herbicides or plant growth regulators which can be combined with the compounds according to the invention are, for example, the following active compounds, where the compounds are designated either with the "common name" in accordance with the International Organization for Standardization (ISO) or with the chemical name or with the code number. They always encompass all of the application forms such as, for example, acids, salts, esters and also all isomeric forms such as stereoisomers and optical isomers, even if not explicitly mentioned.

Examples of herbicidal mixing partners are:
acetochlor, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminocyclopyrachlor-potassium, aminocyclopyrachlor-methyl, aminopyralid, amitrole, ammonium sulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyrone, bifenox, bilanafos, bilanafos-sodium, bispyribac, bispyribac-sodium, bromacil, bromobutide, bromofenoxim, bromoxynil, busoxinone, butachlor, butafenacil, butamifos, butenachlor, butralin, butroxydim, butylate, cafenstrol, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clethodim, clodinafop, clodinafop-propargyl, clomazone, clomeprop, clopyralid, cloransulam, cloransulam-methyl, cumyluron, cyanamide, cyanazine, cycloat, cyclosulfamuron, cycloxydim, cyhalofop, cyhalofop-butyl, cyprazine, 2,4-D, -2,4-D-butotyl, -butyl, -dimethylammonium, -diolamine, -ethyl, -2-ethylhexyl, -isobutyl, -isooctyl, -isopropylammonium, -potassium, -triisopropanolammonium and -trolamine, 2,4-DB, 2,4-DB-butyl, -dimethylammonium, -isooctyl, -potassium and -sodium, daimuron (dymron), dalapon, n-decanol, desmedipham, detosyl-pyrazolate (DTP), dicamba, dichlobenil, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, diquat, diquat-dibromide, dithiopyr, diuron, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfon, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet (thiafluamide), flufenpyr, flufenpyr-ethyl, flumetsulam, flumiclorac, flumiclorac-pentyl, flumioxazin, fluometuron, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fluthiamide, fomesafen, foramsulfuron, fosamine, glufosinate, glufosinate-ammonium, glufosinate-P, glufosinate-P-ammonium, glufosinate-P-sodium, glyphosate, glyphosate-isopropylammonium, -diammonium, -dimethylammonium, -potassium, -sodium and -trimesium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, urea sulfate, hexazinone, HW-02, i.e. 1-(dimethoxyphosphoryl)-ethyl-(2,4-dichlorophenoxyl)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, indanofan, indaziflam, iodosulfuron, iodosulfuron-methyl-sodium, ioxynil, ipfencarbazone, isoproturon, isouron, isoxaben, isoxaflutole, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methiopyrsulfuron, methiozolin, methyl isothiocyanate, metobromuron, metolachlor, S-metolachlor, metosulam, metoxuron, metribuzin, metsulfuron, metsulfuron-methyl, molinate, monolinuron, monosulfuron, monosulfuron-ester, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, napropamide, NC-310, i.e. 4-(2,4-dichlorobenzoyl)-1-methyl-5-benzyloxypyrazole, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat-dichloride, pebulate, pendimethalin, penoxsulam, pentachlorophenol, pentoxazone, pethoxamid, petroleum oils, phenmedipham, picloram, picolinafen, pinoxaden, piperophos, pretilachlor, primisulfuron, primisulfuron-methyl, prodiamine, prifluraline, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfon, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryne, sulcotrione, sulfentrazone, sulfometuron, sulfometuron-methyl, sulfosate (glyphosate-trimesium), sulfosulfuron, SW-065, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione,
TCA, TCA-sodium, tebuthiuron, tefuryltrion, tembotrione, tepraloxydim, terbacil, terbucarb, terbumeton, terbuthylazine, terbutryn, thenylchlor, thiazopyr, thiencarbazone, thiencarbazone-methyl, thifensulfuron, thifensulfuron-methyl, thiobencarb, topramezone, tralkoxydim, triafamone, triallate, triasulfuron, triaziflam, tribenuron, tribenuron-methyl, triclopyr, trietazine, trifloxysulfuron, trifloxysulfuron-sodium, trifluralin, triflusulfuron, triflusulfuron-methyl, tritosulfuron, vernolate, ZJ-0862, i.e. 3,4-dichloro-N-{2-[(4,6-dimethoxypyrimidin-2-yl)oxy]benzyl}aniline, and also the following compounds:

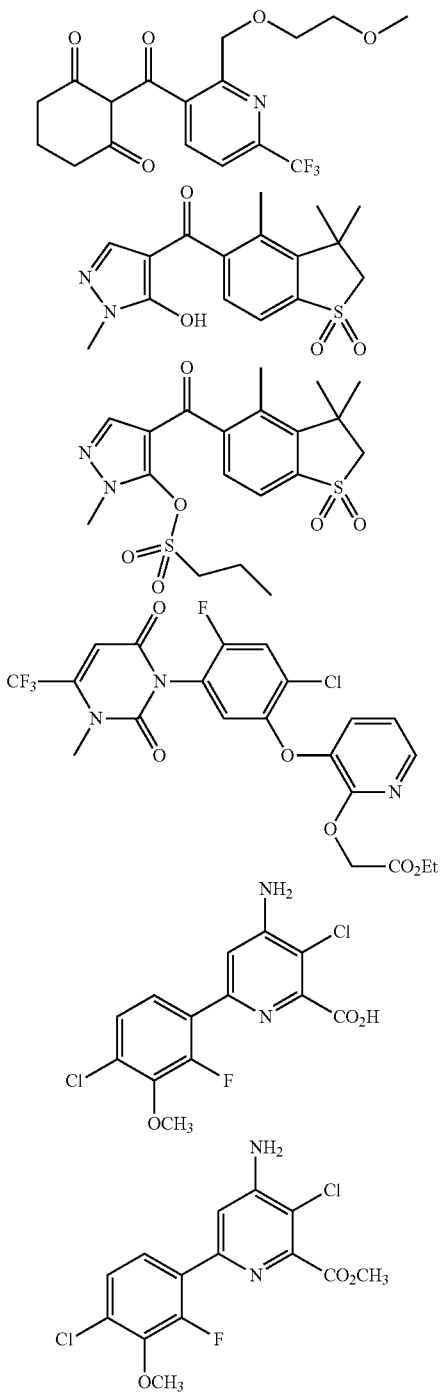

Examples of plant growth regulators as possible mixing partners are:
acibenzolar, acibenzolar-S-methyl, ancymidol, 5-aminolevulinic acid, 6-benzylaminopurine, chlormequat-chloride, cloprop, cyclanilide, 3-(cycloprop-1-enyl)propionic acid, daminozide, dazomet, dikegulac, dikegulac-sodium, ethephon, flumetralin, flurenol, flurenol-butyl, flurprimidol, forchlorfenuron, gibberellic acid, inabenfide, indoleacetic acid (IAA), 4-indol-3-ylbutyric acid, jasmonic acid, ethyl jasmonate, maleic hydrazide, mepiquat-chloride, 1-methylcyclopropene, 2-(1-naphthyl)acetamide, 1-naphthylacetic acid, 2-naphthyloxyacetic acid, nitrophenolate-sodium (isomer mixture), 4-oxo-4[(2-phenylethyl)amino]butyric acid, paclobutrazol, N-phenylphthalamide, prohexadione, prohexadione-calcium, prohydrojasmon, salicylic acid, strigolactone, tecnazene, thidiazuron, triacontanol, trinexapac, trinexapac-ethyl, tsitodef, uniconazole, uniconazole-P.

Of particular interest is the selective control of harmful plants in crops of useful plants and ornamentals. Although the compounds of the general formula (I) according to the invention have already demonstrated very good to adequate selectivity in a large number of crops, in principle, in some crops and in particular also in the case of mixtures with other, less selective herbicides, phytotoxicities on the crop plants may occur. In this connection, combinations of compounds of the general formula (I) according to the invention are of particular interest which comprise the compounds of the general formula (I) or their combinations with other herbicides or pesticides and safeners. The safeners, which are used in an antidotically effective amount, reduce the phytotoxic side effects of the herbicides/pesticides employed, for example in economically important crops, such as cereals (wheat, barley, rye, corn, rice, millet), sugar beet, sugar cane, oilseed rape, cotton and soybeans, preferably cereals. The following groups of compounds are suitable, for example, as safeners for the compounds (I) alone or else in their combinations with further pesticides:

The safeners are preferably selected from the group consisting of:
S1) compounds of the formula (S1)

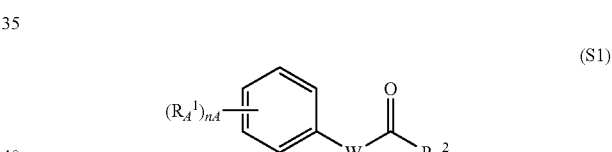

where the symbols and indices have the following meanings:
nA is a natural number from 0 to 5, preferably from 0 to 3;
$R_A^1$ is halogen, $(C_1-C_4)$-alkyl, $(C_1-C_4)$-alkoxy, nitro or $(C_1-C_4)$-haloalkyl;
$W_A$ is an unsubstituted or substituted divalent heterocyclic radical from the group of the partially unsaturated or aromatic five-membered heterocycles having 1 to 3 ring heteroatoms from the N and O group, where at least one nitrogen atom and at most one oxygen atom is present in the ring, preferably a radical from the group of $(W_A^1)$ to $(W_A^4)$;

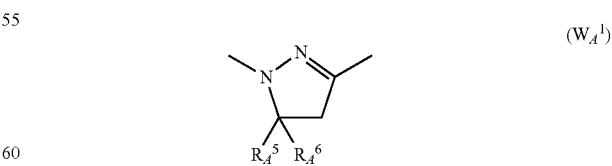

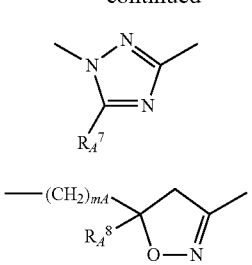

(W$_A^3$)

(W$_A^4$)

mA is 0 or 1;

R$_A^2$ is OR$_A^3$, SR$_A^3$ or NR$_A^3$R$_A^4$ or a saturated or unsaturated 3- to 7-membered heterocycle having at least one nitrogen atom and up to 3 heteroatoms, preferably from the group consisting of O and S, which is joined to the carbonyl group in (S1) via the nitrogen atom and is unsubstituted or substituted by radicals from the group consisting of (C$_1$-C$_4$)-alkyl, (C$_1$-C$_4$)-alkoxy or optionally substituted phenyl, preferably a radical of the formula OR$_A^3$, NHR$_A^4$ or N(CH$_3$)$_2$, especially of the formula OR$_A^3$;

R$_A^3$ is hydrogen or an unsubstituted or substituted aliphatic hydrocarbyl radical preferably having a total of 1 to 18 carbon atoms;

R$_A^4$ is hydrogen, (C$_1$-C$_6$)-alkyl, (C$_1$-C$_6$)-alkoxy or substituted or unsubstituted phenyl;

R$_A^5$ is H, (C$_1$-C$_8$)-alkyl, (C$_1$-C$_8$)-haloalkyl, (C$_1$-C$_4$)-alkoxy-(C$_1$-C$_8$)-alkyl, cyano or COOR$_A^9$ in which R$_A^9$ is hydrogen, (C$_1$-C$_8$)-alkyl, (C$_1$-C$_8$)-haloalkyl, (C$_1$-C$_4$)-alkoxy-(C$_1$-C$_4$)-alkyl, (C$_1$-C$_6$)-hydroxyalkyl, (C$_3$-C$_{12}$)-cycloalkyl or tri-(C$_1$-C$_4$)-alkylsilyl;

R$_A^6$, R$_A^7$, R$_A^8$ are identical or different and are each hydrogen, (C$_1$-C$_8$)-alkyl, (C$_1$-C$_8$)-haloalkyl, (C$_3$-C$_{12}$)-cycloalkyl or substituted or unsubstituted phenyl;

preferably:

a) compounds of the dichlorophenylpyrazoline-3-carboxylic acid type (S1a), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

b) derivatives of dichlorophenylpyrazolecarboxylic acid (S1b), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

c) derivatives of 1,5-diphenylpyrazole-3-carboxylic acid (S1c), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described in EP-A-268 554, for example;

d) compounds of the triazolecarboxylic acid type (S1 d), preferably compounds such as fenchlorazole(-ethyl ester), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;

e) compounds of the 5-benzyl- or 5-phenyl-2-isoxazoline-3-carboxylic acid or of the 5,5-diphenyl-2-isoxazoline-3-carboxylic acid type (S1e), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazolinecarboxylic acid (S1-10) or ethyl 5,5-diphenyl-2-isoxazolinecarboxylate (S1-11) ("isoxadifen-ethyl") or n-propyl 5,5-diphenyl-2-isoxazolinecarboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

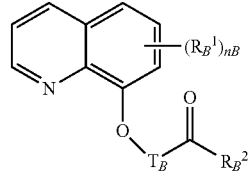

(S2)

where the symbols and indices have the following meanings:

R$_B^1$ is halogen, (C$_1$-C$_4$)-alkyl, (C$_1$-C$_4$)-alkoxy, nitro or (C$_1$-C$_4$)-haloalkyl;

nB is a natural number from 0 to 5, preferably from 0 to 3;

R$_B^2$ is OR$_B^3$, SR$_B^3$ or NR$_B^3$R$_B^4$ or a saturated or unsaturated 3- to 7-membered heterocycle having at least one nitrogen atom and up to 3 heteroatoms, preferably from the group of O and S, which is joined via the nitrogen atom to the carbonyl group in (S2) and is unsubstituted or substituted by radicals from the group of (C$_1$-C$_4$)-alkyl, (C$_1$-C$_4$)-alkoxy or optionally substituted phenyl, preferably a radical of the formula OR$_B^3$, NHR$_B^4$ or N(CH$_3$)$_2$, especially of the formula OR$_B^3$;

R$_B^3$ is hydrogen or an unsubstituted or substituted aliphatic hydrocarbyl radical preferably having a total of 1 to 18 carbon atoms;

R$_B^4$ is hydrogen, (C$_1$-C$_6$)-alkyl, (C$_1$-C$_6$)-alkoxy or substituted or unsubstituted phenyl;

T$_B$ is a (C$_1$ or C$_2$)-alkanediyl chain which is unsubstituted or substituted by one or two (C$_1$-C$_4$)-alkyl radicals or by [(C$_1$-C$_3$)-alkoxy]carbonyl;

preferably:

a) compounds of the 8-quinolinoxyacetic acid type (S2a), preferably 1-methylhexyl(5-chloro-8-quinolinoxy)acetate ("cloquintocet-mexyl") (S2-1), 1,3-dimethylbut-1-yl(5-chloro-8-quinolinoxy)acetate (S2-2), 4-allyloxybutyl(5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), ethyl (5-chloro-8-quinolinoxy)acetate (S2-6), allyl(5-chloro-8-quinolinoxy) acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

b) compounds of the (5-chloro-8-quinolinoxy)malonic acid type (S2b), preferably compounds such as diethyl(5-chloro-8-quinolinoxy)malonate, diallyl(5-chloro-8-quinolinoxy)malonate, methyl ethyl (5-chloro-8-quinolinoxy)malonate and related compounds, as described in EP-A-0 582 198.

S3) Compounds of the formula (S3)

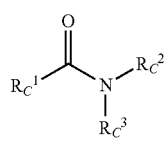

where the symbols and indices have the following meanings:
$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;
$R_C^2$, $R_C^3$ are the same or different and are each hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:
active compounds of the dichloroacetamide type which are frequently used as pre-emergence safeners (soil-active safeners), such as, for example,
"dichlormid" (N,N-diallyl-2,2-dichloroacetamide) (S3-1),
"R-29148" (3-dichloroacetyl-2,2,5-trimethyl-1,3-oxazolidine) from Stauffer (S3-2)
"R-28725" (3-dichloroacetyl-2,2-dimethyl-1,3-oxazolidine) from Stauffer (S3-3),
"benoxacor" (4-dichloroacetyl-3,4-dihydro-3-methyl-2H-1,4-benzoxazine) (S3-4),
"PPG-1292" (N-allyl-N-[(1,3-dioxolan-2-yl)methyl]dichloroacetamide) from PPG Industries (S3-5),
"DKA-24" (N-allyl-N-[(allylaminocarbonyl)methyl]dichloroacetamide) from Sagro-Chem (S3-6),
"AD-67" or "MON 4660" (3-dichloroacetyl-1-oxa-3-azaspiro[4.5]decane) from Nitrokemia or Monsanto (S3-7),
"TI-35" (1-dichloroacetylazepane) from TRI-Chemical RT (S3-8),
"diclonon" (dicyclonon) or "BAS145138" or "LAB145138" (S3-9) ((RS)-1-dichloroacetyl-3,3,8a-trimethylperhydropyrrolo[1,2-a]pyrimidin-6-one) from BASF,
"furilazole" or "MON 13900" ((RS)-3-dichloroacetyl-5-(2-furyl)-2,2-dimethyloxazolidine) (S3-10), and the (R) isomer thereof (S3-11).

S4) N-acylsulfonamides of the formula (S4) and salts thereof,

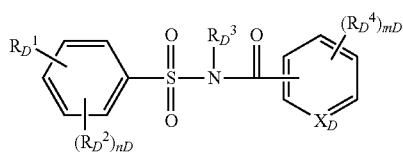

where the symbols and indices have the following meanings:
$X_D$ is CH or N;
$R_D^1$ is CO—$NR_D^5R_D^6$ or NHCO—$R_D^7$;
$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;
$R_D^3$ is hydrogen, $(C_1-C_4)$-alkyl, $(C_2-C_4)$-alkenyl or $(C_2-C_4)$-alkynyl;
$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;
$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl containing vD heteroatoms from the group of nitrogen, oxygen and sulfur, where the seven latter radicals are substituted by vD substituents from the group of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;
$R_D^6$ is hydrogen, $(C_1-C_6)$-alkyl, $(C_2-C_6)$-alkenyl or $(C_2-C_6)$-alkynyl, where the three latter radicals are substituted by vD radicals from the group of halogen, hydroxy, $(C_1-C_4)$-alkyl, $(C_1-C_4)$-alkoxy and $(C_1-C_4)$-alkylthio, or
$R_D^5$ and $R_D^6$ together with the nitrogen atom carrying them form a pyrrolidinyl or piperidinyl radical;
$R_D^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 latter radicals are substituted by vD substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;
nD is 0, 1 or 2;
mD is 1 or 2;
vD is 0, 1, 2 or 3;
among these, preference is given to compounds of the N-acylsulfonamide type, for example of the formula (S4$^a$) below, which are known, for example, from WO-A-97/45016

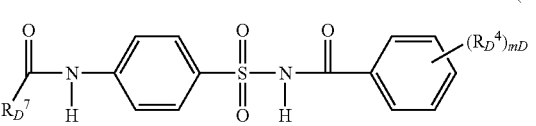

in which
$R_D^7$ is $(C_1-C_6)$-alkyl, $(C_3-C_6)$-cycloalkyl, where the 2 latter radicals are substituted by vD substituents from the group of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;
$R_D^4$ is halogen, $(C_1-C_4)$-alkyl, $(C_1-C_4)$-alkoxy, $CF_3$,
mD is 1 or 2;
vD is 0, 1, 2 or 3;
and
acylsulfamoylbenzamides, for example of the formula (S4$^b$) below, which are known, for example, from WO-A-99/16744,

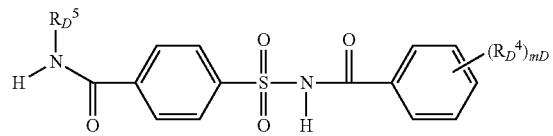

for example those in which
$R_D^5$=cyclopropyl and $(R_D^4)$=2-OMe ("cyprosulfamide", S4-1),
$R_D^5$=cyclopropyl and $(R_D^4)$=5-Cl-2-OMe (S4-2), $R_D{}^5$=ethyl and $(R_D{}^4)$=2-OMe (S4-3),
$R_D{}^5$=isopropyl and $(R_D{}^4)$=5-Cl-2-OMe (S4-4) and
$R_D{}^5$=isopropyl and $(R_D{}^4)$=2-OMe (S4-5)
and
compounds of the N-acylsulfamoylphenylurea type, of the formula (S4$^c$), which are known, for example, from EP-A-365484,

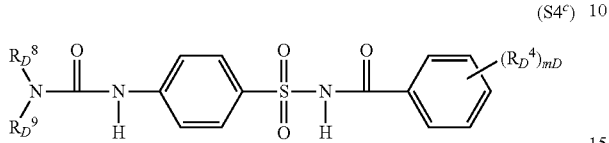

(S4$^c$)

in which
$R_D{}^8$ and $R_D{}^9$ are each independently hydrogen, $(C_1-C_8)$-alkyl, $(C_3-C_8)$-cycloalkyl, $(C_3-C_6)$-alkenyl, $(C_3-C_6)$-alkynyl,
$R_D{}^4$ is halogen, $(C_1-C_4)$-alkyl, $(C_1-C_4)$-alkoxy, $CF_3$
mD is 1 or 2;
for example
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea.

S5) Active compounds from the class of the hydroxyaromatics and the aromatic-aliphatic carboxylic acid derivatives (S5), for example
ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856,

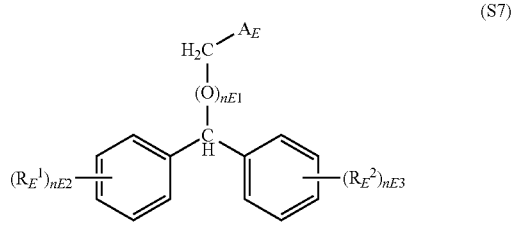

(S7)

where the symbols and indices have the following meanings:
$R_E{}^1$, $R_E{}^2$ are each independently halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;
$A_E$ is $COOR_E{}^3$ or $COSR_E{}^4$
$R_E{}^3$, $R_E{}^4$ are each independently hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl and alkylammonium,
nE1 is 0 or 1;
nE2, nE3 are each independently 0, 1 or 2,
preferably:
diphenylmethoxyacetic acid,
ethyl diphenylmethoxyacetate,
methyl diphenylmethoxyacetate (CAS reg. no. 41858-19-9) (S7-1).

S8) Compounds of the formula (S8), as described in WO-A-98/27049,

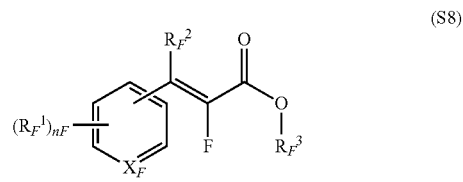

(S8)

in which
$X_E$ is CH or N,
nF in the case that $X_F$=N is an integer from 0 to 4 and in the case that $X_F$=CH is an integer from 0 to 5,
$R_F{}^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulfonyl, $(C_1-C_4)$-alkoxycarbonyl, optionally substituted phenyl, optionally substituted phenoxy,
$R_F{}^2$ is hydrogen or $(C_1-C_4)$alkyl,
$R_F{}^3$ is hydrogen, $(C_1-C_8)$-alkyl, $(C_2-C_4)$-alkenyl, $(C_2-C_4)$-alkynyl, or aryl, where each of the aforementioned carbon-containing radicals is unsubstituted or substituted by one or more, preferably up to three identical or different radicals from the group consisting of halogen and alkoxy; or salts thereof,
preferably compounds in which
$X_E$ is CH,
nF is an integer from 0 to 2,
$R_F{}^1$ is halogen, $(C_1-C_4)$-alkyl, $(C_1-C_4)$-haloalkyl, $(C_1-C_4)$-alkoxy, $(C_1-C_4)$-haloalkoxy,
$R_F{}^2$ is hydrogen or $(C_1-C_4)$-alkyl,
$R_F{}^3$ is hydrogen, $(C_1-C_4)$-alkyl, $(C_2-C_4)$-alkenyl, $(C_2-C_4)$-alkynyl, or aryl, where each of the aforementioned carbon-containing radicals is unsubstituted or substituted by one or more, preferably up to three identical or different radicals from the group consisting of halogen and alkoxy, or salts thereof.

S9) Active compounds from the class of the 3-(5-tetrazolylcarbonyl)-2-quinolones (S9), for example
1,2-dihydro-4-hydroxy-1-ethyl-3-(5-tetrazolylcarbonyl)-2-quinolone (CAS reg. no. 219479-18-2), 1,2-dihydro-4-hydroxy-1-methyl-3-(5-tetrazolylcarbonyl)-2-quinolone (CAS reg. no. 95855-00-8), as described in WO-A-1999/000020.

S10) Compounds of the formulae (S10$^a$) or (S10b) as described in WO-A-2007/023719 and WO-A-2007/023764,

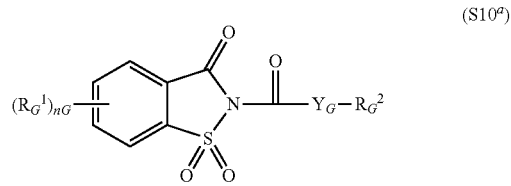

(S10$^a$)

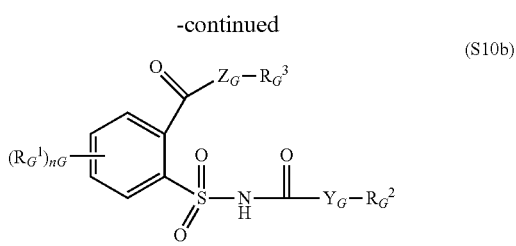
(S10b)

in which
R$_G^1$ is halogen, (C$_1$-C$_4$)-alkyl, methoxy, nitro, cyano, CF$_3$, OCF$_3$,
Y$_G$, Z$_G$ are each independently of one another O or S,
nG is an integer from 0 to 4,
R$_G^2$ is (C$_1$-C$_{16}$)-alkyl, (C$_2$-C$_6$)-alkenyl, (C$_3$-C$_6$)-cycloalkyl, aryl; benzyl, halobenzyl,
R$_G^3$ is hydrogen or (C$_1$-C$_6$)-alkyl.

S11) Active compounds of the oxyimino compound type (S11), which are known as seed-dressing agents, for example
"oxabetrinil" ((Z)-1,3-dioxolan-2-ylmethoxyimino(phenyl)acetonitrile) (S11-1), which is known as a seed-dressing safener for millet/sorghum against metolachlor damage,
"fluxofenim" (1-(4-chlorophenyl)-2,2,2-trifluoro-1-ethanone O-(1,3-dioxolan-2-ylmethyl)oxime) (S11-2), which is known as a seed-dressing safener for millet/sorghum against metolachlor damage, and
"cyometrinil" or "CGA-43089" ((Z)-cyanomethoxyimino(phenyl)acetonitrile) (S11-3), which is known as a seed-dressing safener for millet/sorghum against metolachlor damage.

S12) Active compounds from the class of the isothiochromanones (S12), for example
methyl [(3-oxo-1H-2-benzothiopyran-4(3H)-ylidene)methoxy]acetate (CAS reg. no. 205121-04-6) (S12-1) and related compounds from WO-A-1998/13361.

S13) One or more compounds from group (S13):
"naphthalic anhydride" (1,8-naphthalenedicarboxylic anhydride) (S13-1), which is known as a seed-dressing safener for corn against thiocarbamate herbicide damage,
"fenclorim" (4,6-dichloro-2-phenylpyrimidine) (S13-2), which is known as a safener for pretilachlor in sown rice,
"flurazole" (benzyl 2-chloro-4-trifluoromethyl-1,3-thiazole-5-carboxylate) (S13-3), which is known as a seed-dressing safener for millet, sorghum against alachlor and metolachlor damage,
"CL 304415" (CAS reg. no. 31541-57-8) (4-carboxy-3,4-dihydro-2H-1-benzopyran-4-acetic acid) (S13-4) from American Cyanamid, which is known as a safener for corn against damage by imidazolinones,
"MG 191" (CAS reg. no. 96420-72-3) (2-dichloromethyl-2-methyl-1,3-dioxolane) (S13-5) from Nitrokemia, which is known as a safener for corn,
"MG-838" (CAS reg. no. 133993-74-5) (2-propenyl 1-oxa-4-azaspiro[4.5]decane-4-carbodithioate) (S13-6) from Nitrokemia,
"disulfoton" (O,O-diethyl S-2-ethylthioethyl phosphorodithioate) (S13-7),
"dietholate" (O,O-diethyl O-phenyl phosphorothioate) (S13-8),
"mephenate" (4-chlorophenyl methylcarbamate) (S13-9).

S14) Active compounds which, in addition to herbicidal action against harmful plants, also have safener action on crop plants such as rice, for example
"dimepiperate" or "MY-93" (S-1-methyl 1-phenylethylpiperidine-1-carbothioate), which is known as a safener for rice against damage by the herbicide molinate,
"daimuron" or "SK 23" (1-(1-methyl-1-phenylethyl)-3-p-tolylurea), which is known as safener for rice against imazosulfuron herbicide damage,
"cumyluron"="JC-940" (3-(2-chlorophenylmethyl)-1-(1-methyl-1-phenylethyl)urea, see JP-A-60087254), which is known as safener for rice against damage by some herbicides,
"methoxyphenone" or "NK 049" (3,3'-dimethyl-4-methoxybenzophenone), which is known as safener for rice against damage by some herbicides,
"CSB" (1-bromo-4-(chloromethylsulfonyl)benzene) from Kumiai, (CAS reg. no. 54091-06-4), which is known as a safener against damage by some herbicides in rice.

S15) Active compounds which are used primarily as herbicides but also have safener action on crop plants, for example
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl-3,6-dichloro-2-methoxybenzoate (lactidichlor-ethyl).

Some of the safeners are already known as herbicides and accordingly, in addition to the herbicidal action against harmful plants, also act by protecting the crop plants.

The weight ratios of herbicide (mixture) to safener depend generally on the herbicide application rate and the efficacy of the safener in question and may vary within wide limits, for example in the range from 200:1 to 1:200, preferably 100:1 to 1:100, in particular 20:1 to 1:20. Analogously to the compounds of the formula (I) or mixtures thereof, the safeners can be formulated with further herbicides/pesticides and be provided and employed as a finished formulation or tank mix with the herbicides.

For application, the formulations present in commercial standard form are, if appropriate, diluted in a customary manner, for example with water in the case of wettable powders, emulsifiable concentrates, dispersions and water-dispersible granules. Dust-type formulations, granules for soil application or granules for scattering and sprayable solutions are not normally diluted further with other inert substances prior to application.

The required application rate of the compounds of the general formula (I) varies according to the external conditions such as, inter alia, temperature, humidity and the type of herbicide used. It can vary within wide limits, for example between 0.001 and 10.0 kg/ha or more of active substance, but it is preferably between 0.005 and 5 kg/ha.

The present invention is illustrated in more detail by the examples below; however, these examples do not limit the invention in any way.

A. Synthesis Examples

5-[(6-Ethyl-3,4-dihydro-2H-chromen-4-yl)amino]pyrimidine-2-carbonitrile (Ex.: 64)

0.20 g (1.09 mmol) of 5-bromo-2-cyanopyrimidine (ABCR 245244), 0.325 g (1.52 mmol) of 6-ethyl-3,4-dihydro-2H-chromen-4-aminium chloride and 0.35 g (3.3 mmol) of triethylamine in 1.5 ml of N,N-dimethylacetamide are heated in a closed cuvette in the microwave at 200° C. for 120 minutes (Biotage Initiator, http://www.biotage.com/DynPage.aspx?id=22001). The crude mixture obtained in this manner is applied to silica gel and purified by column chromatography using the mobile phase heptane/ethyl acetate. Concentration gives 0.03 g of 5-[(6-ethyl-3,4-dihydro-2H-chromen-4-yl)amino]pyrimidine-2-carbonitrile (wax-like) (yield 8% at a purity of 80%).

N-(3,4-Dihydro-2H-chromen-4-yl)-2-(methylsulfonyl)pyrimidine-5-amine (Ex.: 92)

0.25 g (1.29 mmol) of 5-chloro-2-(methylsulfonyl)pyrimidine, 0.27 g (1.42 mmol) of 3,4-dihydro-2H-chromene-4-amine hydrochloride and 0.42 g (3.89 mmol) of triethylamine in 1.5 ml of N,N-dimethylacetamide are heated in a closed cuvette in the microwave at 180° C. for 125 minutes (Biotage Initiator, http://www.biotage.com/DynPage.aspx?id=22001). The crude mixture obtained in this manner is applied to silica gel and purified by column chromatography using the mobile phase heptane/ethyl acetate. Concentration gives initially 0.08 g of 5-chloro-2-{[(1R,2S)-2,6-dimethyl-2,3-dihydro-1H-inden-1-yl]amino}pyrimidine-4-carboxamide (wax-like) and then 0.09 g of N-(3,4-dihydro-2H-chromen-4-yl)-2-(methylsulfonyl)pyrimidine-5-amine (wax-like, yield 19% at a purity of 85%).

5-{[(1R,2S)-2,6-Dimethyl-2,3-dihydro-1H-inden-1-yl]amino}-2-(methylsulfonyl)pyrimidine-4-carboxamide (Ex.: 93)

With stirring, 15 g of 5-chloro-2-(methylsulfanyl)pyrimidine-4-carboxylic acid were added a little at a time to 40.8 g (25 ml, 0.34 mol) of thionyl chloride and 0.47 g (0.5 ml, 6.5 mmol) of N,N-dimethylformamide, and the reaction mixture was then heated under reflux until a marked evolution of gas was no longer noticeable. The mixture is taken up in a little methylene chloride. Concentration gives 15 g of 5-chloro-2-(methylsulfanyl)pyrimidine-4-carbonyl chloride, which was used in the next step without further purification.

15 g (67.2 mmol) of 5-chloro-2-(methylsulfanyl)pyrimidine-4-carbonyl chloride are dissolved in 35 ml of dioxane and cooled to 5° C. 57.3 g (0.4 mol) of 7N ammonia in methanol (about 12% strength solution) are slowly added dropwise to the cooled solution. During the addition, the reaction temperature was kept below 15° C. After the dropwise addition had ended, the reaction mixture was allowed to warm to room temperature and stirred for about 15 hours. The mixture was then added to water and the precipitated 5-chloro-2-(methylsulfanyl)pyrimidine-4-carboxamide was isolated (7.7 g, yield 53% at a purity of 95%).

7.7 g (37.8 mmo) of 5-chloro-2-(methylsulfanyl)pyrimidine-4-carboxamide and 37.2 g (60.4 mmol) of potassium peroxomonosulfate are suspended in a mixture of 30 ml of water, 30 ml of acetic acid and 30 ml of methanol, and the mixture is stirred for about 3 hours. The mixture is then taken up in about 100 ml of water and extracted with ethyl acetate. Drying and concentrating of the ethyl acetate extract gave 1.5 g of 5-chloro-2-(methylsulfonyl)pyrimidine-4-carboxamide (melting point 205° C., 17% yield at a purity of 95%). More 5-chloro-2-(methylsulfonyl)pyrimidine-4-carboxamide was able to be isolated from the mother liquor.

0.30 g (1.27 mmol) of 5-chloro-2-(methylsulfonyl)pyrimidine-4-carboxamide, 0.25 g (1.53 mmol) of (1R,2S)-2,6-dimethyl-2,3-dihydro-1H-inden-1-amine and 0.28 g (2.54 mmol) of triethylamine in 1.5 ml of N,N-dimethylacetamide are heated in a closed cuvette in the microwave at 120° C. for 45 minutes (Biotage Initiator, http://www.biotage.com/DynPage.aspx?id=22001). The crude mixture obtained in this manner is applied to silica gel and purified by column chromatography using the mobile phase heptane/ethyl acetate. Concentration gives initially 0.07 g of 5-chloro-2-{[(1R,2S)-2,6-dimethyl-2,3-dihydro-1H-inden-1-yl]amino}pyrimidine-4-carboxamide (wax-like) and then 0.252 g of 5-{[(1R,2S)-2,6-dimethyl-2,3-dihydro-1H-inden-1-yl]amino}-2-(methylsulfonyl)pyrimidine-4-carboxamide (yield 52% at a purity of 95%).

N-[(1R)-2,3-Dihydro-1H-inden-1-yl]-2-(trifluoromethyl)pyrimidine-5-amine (Ex.: 115)

0.20 g (1.20 mmol) of 5-fluoro-2-(trifluoromethyl)pyrimidine, 0.225 g (1.69 mmol) of (1R)-2,3-dihydro-1H-inden-1-amine and 0.50 g (2.41 mmol) of dicyclohexylmethylamine in 1.5 ml of 1-methyl-2-pyrrolidone are heated in a closed cuvette in the microwave at 180° C. for 120 minutes (Biotage Initiator, http://www.biotage.com/DynPage.aspx?id=22001). The crude mixture obtained in this manner is applied to silica gel and purified by column chromatography using the mobile phase heptane/ethyl acetate. Concentration gives 0.34 g of N-[(1R)-2,3-dihydro-1H-inden-1-yl]-2-(trifluoromethyl)pyrimidine-5-amine (melting point 123.7° C., yield 96% at a purity of 95%).

2-(Methylsulfonyl)-N-[(1R)-1,2,3,4-tetrahydronaphthalen-1-yl]pyrimidine-5-amine (Ex.: 273)

0.20 g (0.84 mmol) of 5-chloro-2-(methylsulfonyl)pyrimidine-4-carboxylic acid, 0.15 g (1.01 mmol) of (1R)-1,2,3,4-tetrahydronaphthalene-1-amine and 0.33 g (1.69 mmol) of dicyclohexylmethylamine in 1.5 ml of N-methylpyrrolidone are heated in a closed cuvette in the microwave at 150° C. for 30 minutes (Biotage Initiator, http://www.biotage.com/DynPage.aspx?id=22001). The crude mixture obtained in this manner is applied to silica gel and purified by column chromatography using the mobile phase heptane/ethyl acetate. Concentration gives initially 0.024 g of 5-chloro-N-[(1R)-1,2,3,4-tetrahydronaphthalen-1-yl]pyrimidine-2-amine (solid) and then 0.08 g of 2-(methylsulfonyl)-N-[(1R)-1,2,3,4-tetrahydronaphthalen-1-yl]pyrimidine-5-amine (wax-like, yield 31% at a purity of 95%).

Physicochemical Characterization of Selected Synthesis Examples

| Compound | Description |
|---|---|
| 62 | wax-like; logp (HCOOH): 4.06; 1H-NMR (CDCl$_3$, 400 MHZ, δ in ppm): 2.10-2.35 (m, 2H, 2H of CH$_2$); 2.15 (s, 3H, CH$_3$); 2.20 (s, 3H, CH$_3$); 4.15-4.35 (m, 2H, 2H of CH$_2$O); 5.05 (q, 1H, CH); 5.80 (br, 1H, NH); 6.90 (s and s, 2H, Ar—H); 8.15 (br, 2H, Pyr—H); |
| 64 | wax-like; logp (HCOOH): 2.80; 1H-NMR (CDCl$_3$, 400 MHZ, δ in ppm): 1.20 (t, 3H, CH$_3$); 2.10 (m, 1H, 1H of CH$_2$); 2.30 (m, 1H, 1H of CH$_2$); 2.55 (t, 2H, CH$_2$); 4.15 (m, 1H, 1H of CH$_2$O); 4.30 (m, 1H, 1H of CH$_2$O); 5.7 (br, 1H, CH); 6.80-7.10 (m, 3H, Ar—H); 8.20 (s, 2H, Pyr—H); |

| Compound | Description |
|---|---|
| 65 | wax-like; logp (HCOOH): 2.54; 1H-NMR (CDCl$_3$, 400 MHZ, δ in ppm): 1.20 (t, 3H, CH$_3$); 2.10 (m, 1H, 1H of CH$_2$); 2.25 (m, 1H, 1H of CH$_2$); 2.55 (t, 2H, CH$_2$); 3.10 (s, 3H, SO$_2$CH$_3$); 4.15 (m, 1H, 1H of CH$_2$O); 4.30 (m, 1H, 1H of CH$_2$O); ); 5.25 (q, 1H, CH); 6.30 (br, 1H, NH); 6.80 (d, 1H, Ar—H); 7.05 (s, 1H, Ar—H); 7.10 (d, 1H, Ar—H); 8.55 and 8.80 (s, 2H, Pyr—H); |
| 66 | wax-like; logp (HCOOH): 2.54; 1H-NMR (CDCl$_3$, 400 MHZ, δ in ppm): 1.15 (t, 3H, CH$_3$); 2.10 (m, 1H, 1H of CH$_2$); 2.25 (m, 1H, 1H of CH$_2$); 2.55 (t, 2H, CH$_2$); 3.25 (s, 3H, SO$_2$CH$_3$); 4.15 (m, 1H, 1H of CH$_2$O); 4.25 (m, 1H, 1H of CH$_2$O); ); 5.25 (q, 1H, CH); 6.40 (br, 1H, NH); 6.80 (d, 1H, Ar—H); 7.00 (s, 1H, Ar—H); 7.10 (d, 1H, Ar—H); 8.80 and 8.90 (s, 2H, Pyr—H); |
| 70 | wax-like; logp (HCOOH): 3.41; 1H-NMR (CDCl$_3$, 400 MHZ, δ in ppm): 1.15 (t, 3H, CH$_3$); 2.05 (m, 1H, 1H of CH$_2$); 2.20 (m, 1H, 1H of CH$_2$); 2.55 (t, 2H, CH$_2$); 4.15 (m, 1H, 1H of CH$_2$O); 4.25 (m, 1H, 1H of CH$_2$O); ); 4.50 (br, 1H, NH); 4.70 (q, 1H, CH); 6.80 (d, 1H, Ar—H); 7.05 (s, 1H, Ar—H); 7.10 (d, 1H, Ar—H); 8.25 (s, 2H, Pyr—H); |
| 76 | wax-like; logp (HCOOH): 3.17; 1H-NMR (CDCl$_3$, 400 MHZ, δ in ppm): 1.25 (d, 3H, CH$_3$); 2.30 (s, 3H, CH$_3$); 2.35 (jm, 1H, 1H of CH$_2$); 2.55 (m, 1H, 1H of CH$_2$); 3.15 (q, 1H, 1H of CHCH$_3$); 4.50 (br, 1H, NH); 4.55 (q, 1H, CH); 7.00 (s, 1H, Ar—H); 7.10 (d, 1H, Ar—H); 7.15 (d, 1H, Ar—H); 8.20 (s, 2H, Pyr—H); |
| 83 | solid; 1H-NMR (CDCl$_3$, 400 MHZ, δ in ppm): 1.85 (m, 2H, 2H of CH$_2$); 2.00 (m, 2H, 2H of CH$_2$); 2.80 (m, 2H, 2H of CH$_2$); 4.50 (d, 1H, NH); 4.70 (q, 1H, CH); 7.15-7.25 (m, 4H, Ar—H); 8.15 (s, 2H, Pyr—H); |
| 87 | wax-like; logp (HCOOH): 1.86; 1H-NMR (CDCl$_3$, 400 MHZ, δ in ppm): 1.85 (m, 2H, 2H of CH$_2$); 2.00 (m, 2H, 2H of CH$_2$); 2.80 (m, 2H, 2H of CH$_2$); ); 3.50 (s, 3H, SO$_2$CH$_3$); 5.40 (br, 1H, CH); 5.8 (br, 1H, NH); 6.9 (br, 1H, NH$_2$); 7.15-7.25 (m, 4H, Ar—H); 8.90 and 9.00 (2s, 2H, Pyr—H); |
| 92 | Wax-like; 1H-NMR (CDCl$_3$, 400 MHZ, δ in ppm): 2.10 (m, 1H, 1H of CH$_2$); 2.25 (m, 1H, 1H of CH$_2$); 3.05 (s, 3H, SO$_2$CH$_3$); 4.20 (m, 1H, 1H of CH$_2$O); 4.30 (m, 1H, 1H of CH$_2$O); ); 5.35 (q, 1H, CH); 6.30 (br, 1H, NH); 6.90 (m, 2H, Ar—H); 7.25 (m, 2H, Ar—H); 8.55 and 8.80 (s, 2H, Pyr—H); |
| 93 | wax-like; logp (HCOOH): 2.21; 1H-NMR (CDCl$_3$, 400 MHZ, δ in ppm): 1.25 (d, 3H, CH$_3$); 2.30 (s, 3H, CH$_3$); 2.35 (jm, 1H, 1H of CH$_2$); 2.55 (m, 1H, 1H of CH$_2$); 3.10 (q, 1H, 1H of CHCH$_3$); 3.50 (s, 3H, SO$_2$CH$_3$); 5.20 and 5.40 (in each case t, 1H, CH); 5.90 and 6.20 (in each case d, 1H, NH); ); 6.85 (br, 2H, NH$_2$); 7.00-7.15 (m, 3H, Ar—H); 8.90 and 9.00 (in each case s, 1H, Pyr—H); |
| 108 | solid; logp (HCOOH): 3.29; 1H-NMR (CDCl$_3$, 400 MHZ, δ in ppm): 1.25 (d, 3H, CH$_3$); 2.35 (s, 3H, CH$_3$); 2.35 (m, 1H, 1H of CH$_2$); 2.60 (m, 1H, 1H of CH$_2$); 3.10 (q, 1H, 1H of CHCH$_3$); 3.30 (s, 3H, SO$_2$CH$_3$); 5.20 (m, 1H, CH); 6.05 (br, 1H, NH); 6.95-7.15 (m, 3H, Ar—H); 8.85 and 9.00 (in each case s, 1H, Pyr—H); |
| 109 | solid; logp (HCOOH): 2.97; 1H-NMR (CDCl$_3$, 400 MHZ, δ in ppm): 1.90 (m, 3H, 1H of CH$_2$, 2H of CH$_2$); 2.15 (m, 1H, 1H of CH$_2$); 2.85 (m, 2H, 2H of CH$_2$); 3.30 (s, 3H, SO$_2$CH$_3$); 5.35 (m, 1H, CH); 6.20 (br, 1H, NH); 7.10-7.25 (m, 4H, Ar—H); 8.80 and 9.00 (in each case s, 1H, Pyr—H); |
| 111 | solid; 1H-NMR (CDCl$_3$, 400 MHZ, δ in ppm): 1.95 (m, 1H, 1H of CH$_2$); 2.30 (s, 3H, CH$_3$); 2.65 (m, 1H, 1H of CH$_2$); 2.95 (m, 1H, 1H of CH$_2$); 3.05 (m, 1H, 1H of CH$_2$); 4.40 (d, 1H, NH); 5.05 (q, 1H, CH); 7.10-7.2 (m, 3H, Ar—H); 8.25 (s, 2H, Pyr—H); |
| 115 | solid; Smp.: 123-124° C.; logp (HCOOH): 3.05; 1H-NMR (CDCl$_3$, 400 MHZ, δ in ppm): 1.95 (m, 1H, 1H of CH$_2$); 2.65 (m, 1H, 1H of CH$_2$); 2.90 (m, 1H, 1H of CH$_2$); 3.00 (m, 1H, 1H of CH$_2$); 4.40 (d, 1H, NH); 5.05 (q, 1H, CH); 7.10 -7.20 (m, 4H, Ar—H); 8.20 (s, 2H, Pyr—H); |
| 116 | solid; Smp.: 83-84° C.; logp (HCOOH): 3.79; 1H-NMR (CDCl$_3$, 400 MHZ, δ in ppm): 1.25 (d, 3H, CH$_3$); 2.30 (s, 3H, CH$_3$); 2.35 (m, 1H, 1H of CH$_2$); 2.60 (m, 1H, 1H of CH$_2$); 3.10 (q, 1H, 1H of CHCH$_3$); 4.35 (d, 1H, NH); 4.55 (q, 1H, CH); 7.05 (s, 1H, Ar—H); 7.15 (dd, 2H, Ar—H); 8.25 (s, 2H, Pyr—H); |
| 117 | solid; Smp.: 152-153° C.; logp (HCOOH): 3.45; 1H-NMR (CDCl$_3$, 400 MHZ, δ in ppm): 1.85 (m, 2H, 2H of CH$_2$); 2.05 (m, 2H, 2H of CH$_2$); 2.85 (m, 2H, 2H of CH$_2$); 4.40 (d, 1H, NH); 4.70 (q, 1H, CH); 7.10-7.30 (m, 4H, Ar—H); 8.20 (s, 2H, Pyr—H); |
| 131 | solid; logp (HCOOH): 2.13; 1H-NMR (CDCl$_3$, 400 MHZ, δ in ppm): 1.95 (m, 1H, 1H of CH$_2$); 2.70 (m, 1H, 1H of CH$_2$); 2.90 (m, 1H, 1H of CH$_2$); 3.05 (m, 1H, 1H of CH$_2$); 3.10 (s, 3H, SO$_2$CH$_3$); 5.65 (q, 1H, CH); 6.30 (d, 1H, NH); 7.15-7.30 (m, 4H, Ar—H); 8.50 and 8.80 (in each case s, 1H, Pyr—H); |
| 134 | solid; Smp.: 182-183° C.; logp (HCOOH): 2.83; 1H-NMR (CDCl$_3$, 400 MHZ, δ in ppm): 1.25 (d, 3H, CH$_3$); 2.30 (s, 3H, CH$_3$); 2.35 (m, 1H, 1H of CH$_2$); 2.50 (m, 1H, 1H of CH$_2$); 3.05 (q, 1H, 1H of CHCH$_3$); 3.10 (s, 3H, SO$_2$CH$_3$); 5.35 (q, 1H, CH); 5.90 (d, 1H, NH); 7.00 (s, 1H, Ar—H); 7.10 (dd, 2H, Ar—H); 8.65 and 8.80 (in each case s, 1H, Pyr—H); |

B. Formulation Examples a) A dusting product is obtained by mixing 10 parts by weight of a compound of the formula (I) and/or salts thereof and 90 parts by weight of talc as inert substance and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.), and grinding the mixture in a ball mill to a fineness of below 5 microns.
d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.
e) Water-dispersible granules are obtained by mixing
  75 parts by weight of a compound of the formula (I) and/or salts thereof,
  10 parts by weight of calcium lignosulfonate,
  5 parts by weight of sodium laurylsulfate,
  3 parts by weight of polyvinyl alcohol and
  7 parts by weight of kaolin, After the treatment, the pots are placed in a greenhouse and kept under good growth conditions for the test plants. The damage to the test plants is assessed visually after a test period of 3 weeks by comparison with untreated controls (herbicidal activity in percent (%): 100% action=the plants have died, 0% action=like control plants).

In the tables below, the following abbreviations are used:
ABUTH: *Abutilon theophrasti* ALOMY: *Alopecurus myosuroides*
AMARE: *Amaranthus retroflexus* ECHCG: *Echinochloa crus-galli*
LOLMU: *Lolium multiflorum* MATIN: *Matricaria inodora*
POLCO: *Polygonum convolvulus* SETVI: *Setaria viridis*
STEME: *Stellaria media* VERPE: *Veronica persica*
VIOTR: Viola tricolor

TABLE 1

| Ex No. | Dosage | Unit | ALOMY | ECHCG | LOLMU | SETVI | ABUTH | AMARE | MATIN | POLCO | STEME | VERPE | VIOTR |
|---|---|---|---|---|---|---|---|---|---|---|---|---|---|
| 65  | 1280 | g/ha | 90  | 100 | 90  | 100 | 100 | 100 | 100 | 100 | 100 | 100 | 100 |
| 66  | 1280 | g/ha |     |     |     |     |     | 100 | 90  | 90  | 100 | 100 | 100 |
| 68  | 1280 | g/ha | 100 | 100 | 90  | 100 | 100 | 100 | 100 | 100 | 100 | 100 | 100 |
| 93  | 1280 | g/ha | 90  | 100 | 90  | 90  |     | 100 | 100 | 100 | 100 | 100 | 100 |
| 131 | 1280 | g/ha |     | 100 |     | 90  |     |     | 100 | 100 | 100 | 100 |     |
| 134 | 1280 | g/ha | 100 | 100 | 100 | 100 | 100 | 100 | 100 | 100 | 100 | 100 | 100 |
| 139 | 1280 | g/ha | 90  |     | 100 |     |     | 100 | 100 |     | 100 | 100 | 100 | grinding the mixture in a pinned-disk mill, and granulating the powder in a fluidized bed by spray application of water as a granulating liquid.
f) Water-dispersible granules are also obtained by homogenizing and precomminuting
  25 parts by weight of a compound of the formula (I) and/or salts thereof,
  5 parts by weight of sodium 2,2'-dinaphthylmethane-6,6'-disulfonate,
  2 parts by weight of sodium oleoylmethyltaurate,
  1 part by weight of polyvinyl alcohol,
  17 parts by weight of calcium carbonate and
  50 parts by weight of water
  in a colloid mill, then grinding the mixture in a bead mill and atomizing and drying the resulting suspension in a spray tower by means of a one-phase nozzle.

C. Biological Examples

Test Description

1. Pre-Emergence Herbicidal Effect and Crop Plant Compatibility

Seeds of monocotyledonous and dicotyledonous weed plants and crop plants are placed in wood-fiber pots in sandy loam and covered with soil. The inventive compounds, formulated in the form of wettable powders (WP) or as emulsion concentrates (EC), are then applied to the surface of the covering soil as an aqueous suspension or emulsion at a water application rate of 600 to 800 I/ha (converted) with addition of 0.2% wetting agent.

As shown by the results, the compounds according to the invention have good herbicidal pre-emergence activity against a broad spectrum of weed grasses and broad-leaved weeds. The compounds from Table 1, for example, have very good herbicidal activity against harmful plants such as, for example, *Avena fatua, Stellaria media, Echinochloa crus-galli, Lolium multiflorum, Setaria viridis, Abutilon theophrasti, Amaranthus retroflexus* and *Alopecurus myosuroides* when applied by the pre-emergence method at an application rate of 1.28 kg and less of active substance per hectare. Accordingly, the compounds according to the invention are suitable for controlling unwanted plant growth by the pre-emergence method.

2. Post-Emergence Herbicidal Effect and Crop Plant Compatibility

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The compounds according to the invention, formulated in the form of wettable powders (WP) or as emulsion concentrates (EC), are then sprayed as aqueous suspension or emulsion at a water application rate of 600 to 800 I/ha (converted) with the addition of 0.2% of wetting agent onto the green parts of the plants. After the test plants have been kept in the greenhouse under optimum growth conditions for about 3 weeks, the activity of the preparations is rated visually in comparison to untreated controls (herbicidal activity in percent (%): 100% activity=the plants have died, 0% activity=like control plants).

TABLE 2

| Ex. No. | Dosage | Unit | ECHCG | ABUTH | AMARE | POLCO | STEME | VERPE | VIOTR |
|---|---|---|---|---|---|---|---|---|---|
| 65  | 1280 | g/ha | 100 | 90 |    | 80 | 90  |    |    |
| 68  | 1280 | g/ha | 90  | 90 |    | 80 |     |    | 80 |
| 93  | 1280 | g/ha |     | 80 | 80 |    |     |    |    |
| 131 | 1280 | g/ha |     | 80 | 80 | 80 |     | 80 |    |
| 134 | 1280 | g/ha | 90  | 90 | 80 | 90 | 100 | 90 | 90 |

As the results show, inventive compounds have good herbicidal post-emergence efficacy against a broad spectrum of weed grasses and broad-leaved weeds. The compounds from Table 2, for example, have very good herbicidal activity against harmful plants such as, for example, *Avena fatua, Stellaria media, Echinochloa crus-galli, Lolium multiflorum, Setaria viridis, Abutilon theophrasti, Amaranthus retroflexus* and *Alopecurus myosuroides* when applied by the post-emergence method at an application rate of 1.28 kg and less of active substance per hectare. Accordingly, the compounds according to the invention are suitable for controlling unwanted plant growth by the post-emergence method.

The invention claimed is:

1. A compound of formula (I) or an agrochemically acceptable salt thereof

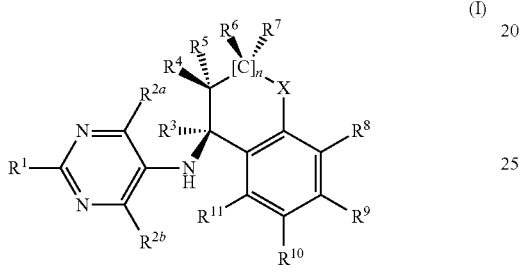

(I)

in which
R$^1$ is selected from the group consisting of
cyano (CN), NO$_2$, (C$_1$-C$_3$)-alkyl, (C$_1$-C$_6$)-haloalkyl, (C$_1$-C$_6$)-alkoxy, (C$_1$-C$_6$)-haloalkoxy, (C$_1$-C$_6$)-alkylthio, (C$_1$-C$_6$)-alkyl sulfoxide, (C$_1$-C$_6$)-alkylsulfonyl, (C$_1$-C$_6$)-haloalkylsulfonyl, (C$_1$-C$_6$)-alkoxy-carbonyl, amino-carbonyl, mono-((C$_1$-C$_6$)-alkyl)-amino-carbonyl, di-((C$_1$-C$_6$)-alkyl)-amino-carbonyl, (C$_6$-C$_{14}$)-aryl, (C$_6$-C$_{14}$)-aryl-haloalkyl, (C$_1$-C$_6$)-aryloxy, (C$_6$-C$_{14}$)-haloaryl-(C$_1$-C$_6$)-alkyl, (C$_2$-C$_6$)-alkynyl-(C$_1$-C$_6$)-alkoxy, (C$_2$-C$_6$)-alkynyl-(C$_1$-C$_6$)-alkyl-(C$_1$-C$_6$)-alkoxy, and (C$_1$-C$_6$)-alkyl-(C$_2$-C$_6$)-alkynyl-(C$_1$-C$_6$)-alkoxy; and
R$^{2a}$ and R$^{2b}$, each independently of one another, are selected from the group consisting of
hydrogen, halogen, hydroxy, cyano, nitro, C(O)OH, C(O)NH$_2$;
(C$_1$-C$_6$)-alkyl, (C$_1$-C$_6$)-haloalkyl, (C$_1$-C$_6$)-alkylcarbonyl, (C$_1$-C$_6$)-haloalkylcarbonyl, (C$_1$-C$_6$)-alkylcarbonyloxy, (C$_1$-C$_6$)-haloalkylcarbonyloxy, (C$_1$-C$_6$)-alkylcarbonyl-(C$_1$-C$_4$)-alkyl;
(C$_1$-C$_6$)-alkoxy, (C$_1$-C$_6$)-haloalkoxy, (C$_1$-C$_6$)-alkoxycarbonyl, (C$_1$-C$_6$)-haloalkoxycarbonyl, (C$_1$-C$_6$)-alkoxycarbonyl-(C$_1$-C$_6$)-alkyl, (C$_1$-C$_6$)-haloalkoxycarbonyl-(C$_1$-C$_6$)-alkyl, (C$_1$-C$_6$)-alkoxycarbonyl-(C$_1$-C$_6$)-haloalkyl, (C$_1$-C$_6$)-haloalkoxycarbonyl-(C$_1$-C$_6$)-haloalkyl;
(C$_2$-C$_6$)-alkenyl, (C$_2$-C$_6$)-haloalkenyl, (C$_2$-C$_6$)-alkenylcarbonyl, (C$_2$-C$_6$)-haloalkenylcarbonyl, (C$_2$-C$_6$)-alkenyloxy, (C$_2$-C$_6$)-haloalkenyloxy, (C$_2$-C$_6$)-alkenyloxycarbonyl, (C$_2$-C$_6$)-haloalkenyloxycarbonyl;
(C$_2$-C$_6$)-alkynyl, (C$_2$-C$_6$)-haloalkynyl, (C$_2$-C$_6$)-alkynylcarbonyl, (C$_2$-C$_6$)-haloalkynylcarbonyl, (C$_2$-C$_6$)-alkynyloxy, (C$_2$-C$_6$)-haloalkynyloxy, (C$_2$-C$_6$)-alkynyloxycarbonyl, (C$_2$-C$_6$)-haloalkynyloxycarbonyl;
tri-(C$_1$-C$_6$)-alkylsilyl-(C$_2$-C$_6$)-alkynyl, di-(C$_1$-C$_6$)-alkylsilyl-(C$_2$-C$_6$)-alkynyl, mono-(C$_1$-C$_6$)-alkylsilyl-(C$_2$-C$_6$)-alkynyl; phenylsilyl-(C$_2$-C$_6$)-alkynyl;
(C$_6$-C$_{14}$)-aryl, (C$_6$-C$_{14}$)-aryloxy, (C$_6$-C$_{14}$)-arylcarbonyl and (C$_6$-C$_{14}$)-aryloxycarbonyl, each of which may be substituted at the aryl moiety by halogen, (C$_1$-C$_6$)-alkyl or (C$_1$-C$_6$)-haloalkyl;
(C$_6$-C$_{14}$)-aryl-(C$_1$-C$_6$)-alkyl, (C$_6$-C$_{14}$)-aryl-(C$_1$-C$_6$)-alkoxy, (C$_6$-C$_{14}$)-aryl-(C$_1$-C$_6$)-alkyl-carbonyl, (C$_6$-C$_{14}$)-aryl-(C$_1$-C$_6$)-alkyl-carbonyloxy, (C$_6$-C$_{14}$)-aryl-(C$_1$-C$_6$)-alkoxycarbonyl, (C$_6$-C$_{14}$)-aryl-(C$_1$-C$_6$)-alkoxycarbonyloxy;
N—((C$_1$-C$_6$)-haloalkanoyl)-amino, aminocarbonyl-(C$_1$-C$_6$)-alkyl, di-(C$_1$-C$_6$)-alkylaminocarbonyl-(C$_1$-C$_6$)-alkyl;
N—((C$_1$-C$_6$)-haloalkanoyl)-amino-carbonyl, mono-((C$_6$-C$_{14}$)-aryl)-amino-carbonyl, di-((C$_6$-C$_{14}$)-aryl)-amino-carbonyl;
(C$_1$-C$_6$)-alkoxy-(C$_1$-C$_6$)-alkyl, (C$_1$-C$_6$)-alkoxy-(C$_1$-C$_6$)-alkoxy, (C$_1$-C$_6$)-alkoxycarbonyl-(C$_1$-C$_6$)-alkoxy;
(C$_3$-C$_8$)-cycloalkyl, which may optionally be substituted at the cycloalkyl radical by (C$_1$-C$_6$)-alkyl or halogen; (C$_3$-C$_8$)-cycloalkoxy, (C$_3$-C$_8$)-cycloalkyl-(C$_1$-C$_6$)-alkyl, (C$_3$-C$_8$)-cycloalkyl-(C$_1$-C$_6$)-haloalkyl, (C$_3$-C$_8$)-cycloalkyl-(C$_1$-C$_6$)-alkoxy, (C$_3$-C$_8$)-cycloalkyl-(C$_1$-C$_6$)-haloalkoxy, (C$_3$-C$_8$)-cycloalkylcarbonyl, (C$_3$-C$_8$)-cycloalkoxycarbonyl, (C$_3$-C$_8$)-cycloalkyl-(C$_1$-C$_6$)-alkylcarbonyl, (C$_3$-C$_8$)-cycloalkyl-(C$_1$-C$_6$)-haloalkylcarbonyl, (C$_3$-C$_8$)-cycloalkyl-(C$_1$-C$_6$)-alkoxycarbonyl, (C$_3$-C$_8$)-cycloalkyl-(C$_1$-C$_6$)-haloalkoxycarbonyl, (C$_3$-C$_8$)-cycloalkylcarbonyloxy, (C$_3$-C$_8$)-cycloalkoxycarbonyloxy, (C$_3$-C$_8$)-cycloalkyl-(C$_1$-C$_6$)-alkylcarbonyloxy, (C$_3$-C$_8$)-cycloalkyl-(C$_1$-C$_6$)-haloalkylcarbonyloxy, (C$_3$-C$_8$)-cycloalkyl-(C$_1$-C$_6$)-alkoxycarbonyloxy, (C$_3$-C$_8$)-cycloalkyl-(C$_1$-C$_6$)-haloalkoxycarbonyloxy;
(C$_3$-C$_8$)-cycloalkenyl, (C$_3$-C$_8$)-cycloalkenyloxy, (C$_3$-C$_8$)-cycloalkenyl-(C$_1$-C$_6$)-alkyl, (C$_3$-C$_8$)-cycloalkenyl-(C$_1$-C$_6$)-haloalkyl, (C$_3$-C$_8$)-cycloalkenyl-(C$_1$-C$_6$)-alkoxy, (C$_3$-C$_8$)-cycloalkenyl-(C$_1$-C$_6$)-haloalkoxy, (C$_3$-C$_8$)-cycloalkenylcarbonyl, (C$_3$-C$_8$)-cycloalkenyloxycarbonyl, (C$_3$-C$_8$)-cycloalkenyl-(C$_1$-C$_6$)-alkylcarbonyl, (C$_3$-C$_8$)-cycloalkenyl-(C$_1$-C$_6$)-haloalkylcarbonyl, (C$_3$-C$_8$)-cycloalkenyl-(C$_1$-C$_6$)-alkoxycarbonyl, (C$_3$-C$_8$)-cycloalkenyl-(C$_1$-C$_6$)-haloalkoxycarbonyl, (C$_3$-C$_8$)-cycloalkenylcarbonyloxy, (C$_3$-C$_8$)-cycloalkenyloxycarbonyloxy, (C$_3$-C$_8$)-cycloalkenyl-(C$_1$-C$_6$)-alkylcarbonyloxy, (C$_3$-C$_8$)-cycloalkenyl-(C$_1$-C$_6$)-haloalkylcarbonyloxy, (C$_3$-C$_8$)-cycloalkenyl-(C$_1$-C$_6$)-alkoxycarbonyloxy, (C$_3$-C$_8$)-cycloalkenyl-(C$_1$-C$_6$)-haloalkoxycarbonyloxy;
hydroxy-(C$_1$-C$_6$)-alkyl, hydroxy-(C$_1$-C$_6$)-alkoxy, cyano-(C$_1$-C$_6$)-alkoxy, cyano-(C$_1$-C$_6$)-alkyl;
(C$_1$-C$_6$)-alkylsulfonyl, (C$_1$-C$_6$)-alkylthio, (C$_1$-C$_6$)-alkylsulfinyl, (C$_1$-C$_6$)-haloalkylsulfonyl, (C$_1$-C$_6$)-haloalkylthio, (C$_1$-C$_6$)-haloalkylsulfinyl, (C$_1$-C$_6$)-alkylsulfonyl-(C$_1$-C$_6$)-alkyl, (C$_1$-C$_6$)-alkylthio-(C$_1$-C$_6$)-alkyl, (C$_1$-C$_6$)-alkylsulfinyl-(C$_1$-C$_6$)-alkyl, (C$_1$-C$_6$)-haloalkylsulfonyl-(C$_1$-C$_6$)-alkyl, (C$_1$-C$_6$)-haloalkylthio-(C$_1$-C$_6$)-alkyl, (C$_1$-C$_6$)-haloalkylsulfinyl-(C$_1$-C$_6$)-alkyl, (C$_1$-C$_6$)-alkylsulfonyl-(C$_1$-C$_6$)-haloalkyl, (C$_1$-C$_6$)-alkylthio-(C$_1$-C$_6$)-haloalkyl, (C$_1$-C$_6$)-alkylsulfinyl-(C$_1$-C$_6$)-haloalkyl, (C$_1$-C$_6$)-haloalkylsulfonyl-(C$_1$-C$_6$)-haloalkyl, (C$_1$-C$_6$)-haloalkylthio-(C$_1$-C$_6$)-haloalkyl, (C$_1$-C$_6$)-haloalkylsulfinyl-(C$_1$-C$_6$)-haloalkyl, (C$_1$-C$_6$)-alkylsulfonyloxy, (C$_1$-C$_6$)-haloalkylsulfonyloxy, ($C_1$-$C_6$)-alkylthiocarbonyl, ($C_1$-$C_6$)-haloalkylthiocarbonyl, ($C_1$-$C_6$)-alkylthiocarbonyloxy, ($C_1$-$C_6$)-haloalkylthiocarbonyloxy, ($C_1$-$C_6$)-alkylthio-($C_1$-$C_6$)-alkyl, ($C_1$-$C_6$)-alkylthio-($C_1$-$C_6$)-alkoxy, ($C_1$-$C_6$)-alkylthio-($C_1$-$C_6$)-alkylcarbonyl, ($C_1$-$C_6$)-alkylthio-($C_1$-$C_6$)-alkylcarbonyloxy; ($C_4$-$C_{14}$)-arylsulfonyl, ($C_6$-$C_{14}$)-arylthio, ($C_6$-$C_{14}$)-arylsulfinyl, ($C_3$-$C_8$)-cycloalkylthio, ($C_3$-$C_8$)-alkenylthio, ($C_3$-$C_8$)-cycloalkenylthio, and ($C_3$-$C_6$)-alkynylthio; and $R^3$ is selected from the group consisting of
hydrogen, cyano, C(O)OH, C(O)$NH_2$;
($C_1$-$C_6$)-alkyl and ($C_1$-$C_6$)-haloalkyl; and
($C_1$-$C_6$)-alkoxycarbonyl; and $R^4$ and $R^5$, each independently of one another, are selected from the group consisting of hydrogen, ($C_1$-$C_6$)-alkyl, ($C_1$-$C_6$)-haloalkyl, hydroxy, ($C_1$-$C_6$)-alkoxy and ($C_1$-$C_6$)-haloalkoxy; or the radicals $R^4$ and $R^5$ together with the carbon atom to which they are attached form a three- to seven-membered ring; and $R^6$ and $R^7$, each independently of one another, are selected from the group consisting of hydrogen, ($C_1$-$C_6$)-alkyl, ($C_1$-$C_6$)-haloalkyl, ($C_1$-$C_6$)-alkoxy, ($C_1$-$C_6$)-haloalkoxy, ($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl; or the radicals $R^6$ and $R^7$ together form a ($C_1$-$C_7$)-alkylene group, which may contain one or more oxygen or sulfur atoms, where the ($C_1$-$C_7$)-alkylene group may be mono- or polysubstituted by halogen and the halogen substituents in question may be identical or different, and n is the number 0, 1 or 2 and $R^8$, $R^9$, $R^{10}$ and $R^{11}$, each independently of one another, are selected from the group consisting of hydrogen, halogen, cyano, C(O)OH, C(O)$NH_2$, ($C_1$-$C_6$)-alkyl, ($C_1$-$C_6$)-alkylcarbonyl, ($C_1$-$C_6$)-alkyloxycarbonyl, ($C_1$-$C_6$)-alkylaminocarbonyl, ($C_1$-$C_6$)-di-alkylaminocarbonyl, ($C_1$-$C_6$)-haloalkyl, ($C_1$-$C_6$)-alkoxy, ($C_1$-$C_6$)-haloalkoxy, ($C_2$-$C_6$)-alkenyl, ($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl and ($C_2$-$C_6$)-haloalkynyloxycarbonyl and nitro;

X is a bond, $CH_2$, O, S, carbonyl, NH, $CR^{12}R^{13}$ or $NR^{14}$ or $CH_2O$, $CH_2S$, where in the two last-mentioned groups the carbon atom is attached to the aromatic moiety and the heteroatom O or S is attached to the partially hydrogenated moiety of the amine; and $R^{12}$ and $R^{13}$, each independently of one another, are selected from the group consisting of hydrogen, ($C_1$-$C_6$)-alkyl and ($C_1$-$C_6$)-haloalkyl; and $R^{14}$ is selected from the group consisting of hydrogen, ($C_1$-$C_6$)-alkyl, and ($C_1$-$C_6$)-haloalkyl.

2. The compound of formula (I) as claimed in claim 1, wherein the radicals $R^{2a}$ and $R^{2b}$, each independently of one another, are selected from the group consisting of hydrogen, CN, hydroxy (OH), ($C_1$-$C_6$)-alkyl, ($C_1$-$C_6$)-haloalkyl, ($C_1$-$C_6$)-cycloalkyl, ($C_1$-$C_6$)-alkoxy, aminocarbonyl, hydroxycarbonyl COOH, ($C_1$-$C_6$)-alkoxycarbonyl, ($C_1$-$C_6$)-alkyl sulfonyl, mono-(($C_1$-$C_6$)-alkyl)-amino-carbonyl, di-(($C_1$-$C_6$)-alkyl)-amino-carbonyl, mono-(($C_6$-$C_{14}$)-aryl)-amino-carbonyl, mono-(($C_2$-$C_6$)-alkylene)-amino-carbonyl, mono-(($C_6$-$C_{14}$)-aryl-($C_1$-$C_6$)-alkyl)-amino-carbonyl, ($C_1$-$C_6$)-alkoxy-($C_1$-$C_6$)-alkoxy-carbonyl and di-(($C_1$-$C_6$)-alkyl)-amino-($C_1$-$C_6$)-alkoxycarbonyl.

3. The compound of formula (I) as claimed in claim 1, wherein the radical $R^3$ is selected from the group consisting of hydrogen, $CH_3$, $CH_2CH_2OCH_3$, $COOCH_3$, $CONH_2$ and $C_6H_5$.

4. The compound of formula (I) as claimed in claim 1, wherein the radicals $R^4$ and $R^5$, each independently of one another, are selected from the group consisting of hydrogen, cyano, hydroxy, ($C_1$-$C_6$)-alkyl and ($C_1$-$C_6$)-alkoxy.

5. The compound of formula (I) as claimed in claim 1, wherein the radicals R4 and R5 are a ($C_1$-$C_3$)-alkylene group and together with the carbon atom to which they are attached form a three- or four-membered ring.

6. The compound of formula (I) as claimed in claim 1, wherein R6 and R7 independently of one another are selected from the group consisting of hydrogen, methyl and phenyl.

7. The compound of formula (I) as claimed in claim 1, wherein the radical $R^8$ is selected from the group consisting of hydrogen, halogen, ($C_1$-$C_6$)-alkyl, ($C_1$-$C_6$)-alkoxy and di-($C_1$-$C_6$)-alkylamino.

8. The compound of formula (I) as claimed in claim 1, wherein the radical $R^9$ is selected from the group consisting of hydrogen, chlorine, fluorine, ($C_1$-$C_6$)-alkyl and ($C_1$-$C_6$)-alkoxy.

9. The compound of formula (I) as claimed in claim 1, wherein the radical $R^{10}$ is selected from the group consisting of hydrogen, fluorine, chlorine, bromine, cyano, $CONH_2$, COOH, methyl ($CH_3$), ethyl ($CH_2CH_3$), methoxy ($OCH_3$), $CH{=}CH_2$, $C{\equiv}CH$ and $C{\equiv}CCH_3$.

10. The compound of formula (I) as claimed in claim 1, wherein the radical $R^{11}$ is selected from the group consisting of hydrogen and methyl.

11. The compound of formula (I) as claimed in claim 1, wherein the radical X is selected from the group consisting of O, S, carbonyl, $CH_2$, NH, $CHCH_3$, $NCH_3$, $C(CH_3)_2$, $OCH_2$, $SCH_2$, and a chemical bond.

12. A process for preparing a compound of formula (I) or an agrochemically acceptable salt thereof or an agrochemically acceptable quaternized nitrogen derivative thereof as claimed in claim 1: comprising reacting
a compound of formula (II)

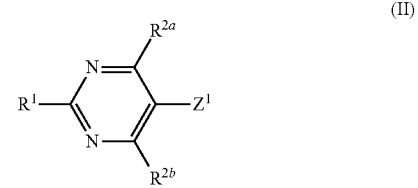

in which $Z^1$ is an exchangeable radical or a leaving group,
with an amine of formula (III) or an acid addition salt of an amine of formula (III)

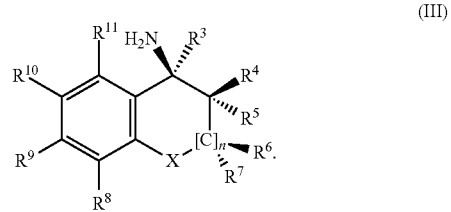

13. The process as claimed in claim 12, where the exchangeable radical or the leaving group $Z^1$ is fluorine, chlorine, bromine, iodine, a $(C_1$-$C_4)$-alkylsulfonyl, an unsubstituted or a substituted phenyl-$(C_1$-$C_4)$-alkylsulfonyl or a $(C_1$-$C_4)$-alkylphenylsulfonyl.

14. A herbicidal or plant growth-regulating composition, comprising one or more compounds of formula (I) or a salt thereof as claimed in claim 1.

15. A method for controlling harmful plants or for regulating growth of plants, comprising applying an effective amount of one or more compounds of formula (I) or salts thereof as claimed in claim 1 onto plants, plant parts, plant seeds or an area under cultivation.

16. The method as claimed in claim 15, wherein the compound is employed for controlling harmful plants or for regulating growth of plants in crops of useful plants or ornamental plants.

17. The method as claimed in claim 16, wherein the plants are transgenic crop plants.

18. The method as claimed in claim 16, wherein the plants are plantation crops.

\* \* \* \* \*